United States Patent
Shnaiderman et al.

(10) Patent No.: US 11,513,282 B2
(45) Date of Patent: Nov. 29, 2022

(54) SENSOR COMPRISING A WAVEGUIDE WITH OPTICAL RESONATOR AND SENSING METHOD

(71) Applicant: TECHNISCHE UNIVERSITÄT MÜNCHEN, Munich (DE)

(72) Inventors: Rami Shnaiderman, Munich (DE); Georg Michael Wissmeyer, Munich (DE); Vasilis Ntziachristos, Gräfelfing (DE)

(73) Assignee: TECHNISCHE UNIVERSITÄT MÜNCHEN, Munich (DE)

(*) Notice: Subject to any disclaimer, the term of this patent is extended or adjusted under 35 U.S.C. 154(b) by 143 days.

(21) Appl. No.: 16/979,044

(22) PCT Filed: Mar. 8, 2019

(86) PCT No.: PCT/EP2019/055897
§ 371 (c)(1),
(2) Date: Sep. 8, 2020

(87) PCT Pub. No.: WO2019/170884
PCT Pub. Date: Sep. 12, 2019

(65) Prior Publication Data
US 2021/0055473 A1   Feb. 25, 2021

(30) Foreign Application Priority Data
Mar. 9, 2018 (EP) .................... 18160946

(51) Int. Cl.
*G02B 6/02* (2006.01)
*A61B 5/00* (2006.01)
(Continued)

(52) U.S. Cl.
CPC ........ *G02B 6/02076* (2013.01); *A61B 5/0095* (2013.01); *G01H 9/004* (2013.01);
(Continued)

(58) Field of Classification Search
CPC ...... G02B 6/02076; G02B 2006/12107; G02B 6/12007; A61B 5/0095; A61B 2562/0233;
(Continued)

(56) References Cited

U.S. PATENT DOCUMENTS 7,054,011 B2   5/2006  Zhu et al.
7,292,755 B1  11/2007  Greiner et al.
(Continued)

FOREIGN PATENT DOCUMENTS

WO    2010/043876    4/2010

OTHER PUBLICATIONS

International Search Report and Written Opinion for PCT Application No. PCT/EP2019/055897 dated May 15, 2019.
(Continued)

*Primary Examiner* — John Bedtelyon
(74) *Attorney, Agent, or Firm* — Branch Partners PLLC; Bruce E. Black

(57) ABSTRACT

A sensor (10) comprises a waveguide (20) having a longitudinal axis and an end face (21), the waveguide (20) comprising a Bragg grating (23). The sensor comprises at least one reflector (24) on the end face (21) of the waveguide (20). An optical resonator (25) is formed by the Bragg grating (23), the at least one reflector (24), and an inner portion of the optical resonator (25) between the Bragg grating (23) and the at least one reflector (24). The inner portion of the optical resonator (25) extends within a portion of the waveguide (20). The sensor (10) comprises a detector (32) configured to detect at least one spectral characteristic of the optical resonator (25) or a change of at least one spectral characteristic of the optical resonator (25).

25 Claims, 9 Drawing Sheets

(51) Int. Cl.
  *G01H 9/00* (2006.01)
  *G01L 11/02* (2006.01)
  *G01N 21/45* (2006.01)

(52) U.S. Cl.
  CPC ............ *G01L 11/025* (2013.01); *G01N 21/45* (2013.01); *G01N 2021/458* (2013.01)

(58) Field of Classification Search
  CPC . A61B 5/02007; A61B 5/0215; A61B 5/1459; A61B 5/6851; A61B 5/6852; A61B 8/12; A61B 8/44; G01H 9/004; G01L 11/025; G01N 21/45; G01N 2021/458
  See application file for complete search history.

(56) References Cited

U.S. PATENT DOCUMENTS

2002/0166955 A1* 11/2002 Ogawa ................... G01H 9/004
                                                   250/227.21
2014/0180030 A1    6/2014 Dorando

OTHER PUBLICATIONS

Extended European Search report for EP Application No. 18160946.2 dated Aug. 24, 2018.
G. Wissmeyer et al., "All-optical optoacoustic microscope based on wideband pulse interferometry," Optics Letters, vol. 41, Issue 9, pp. 1953-1956 (2016).
A. Rosenthal et al., "Embedded ultrasound sensor in a silicon-on-insulator photonic platform," Appl. Phys. Lett. 104, 021116 (2014).
A. Rosenthal et al., "Sensitive interferometric detection of ultrasound for minimally invasive clinical imaging applications," Laser Photonics Rev., vol. 8, No. 3, pp. 450-457 (2014).
C. Zhang et al., "Review of Imprinted Polymer Microrings as Ultrasound Detectors: Design, Fabrication, and Characterization," IEEE Sensors Journal, vol. 15, No. 6 (Jun. 2015).
R. Nuster et al., "Photoacoustic section imaging using an elliptical acoustic mirror and optical detection," JBO Letter, vol. 17(3), 030503 (Mar. 2012).

* cited by examiner

SENSOR COMPRISING A WAVEGUIDE WITH OPTICAL RESONATOR AND SENSING METHOD

CROSS-REFERENCE TO RELATED APPLICATIONS

This present application is a U.S. national stage application of PCT Application No. PCT/EP2019/055897, filed Mar. 8, 2019, which claims priority to European Patent Application No. 18160946.2 filed Mar. 9, 2018, both of which are hereby incorporated by reference in their entirety.

TECHNICAL FIELD

Embodiments of the invention relate to sensors, and to other devices comprising a waveguide and optical resonator. Embodiments of the invention relate in particular to waveguides and optical resonators that can be used in sensors, and to sensors and sensing methods using such waveguides.

BACKGROUND

There is an ever increasing demand for waveguides and optical resonators that lend themselves for new fields of application. For illustration, acoustic sensing, e.g. in the ultrasound frequency range, has frequently been performed using piezoelectric detectors. The current demand for high performance ultrasound sensors cannot be met by such traditional piezoelectric detectors. For illustration, non-destructive testing in harsh environments and the emerging fields of optoacoustic endoscopy and optoacoustic/photoacoustic hybrid microscopy require sensors that are extremely small, flexible and immune to electromagnetic interference, and exhibit high bandwidth. The latter is particularly important as the bandwidth and central frequency of ultrasonic signals generated by the optoacoustic effect is proportional to the optical absorber size.

It would be desirable to have high bandwidth sensors that then could be used to, e.g., differentiate and label absorbers according to their size, such as vasculature under and in the skin. Such improved sensors can help in, e.g., studying and monitoring tumors by studying angiogenesis, and conditions like diabetes, hypertension, etc.

Sensors based on optical resonators are a promising alternative.

WO 2010/043876 A2 discloses a combined pressure and temperature sensor. The sensor comprises at least one first optical sensing element of a first type and at least one second optical sensing element of a second type. The sensor is adapted to compensate for temperature and/or pressure effects in the first or second optical sensing element using a response of the other of the second or first optical sensing elements. An optical cavity may be formed in a gap between two fiber ends.

U.S. Pat. No. 7,054,011 B2 discloses a fiber optic sensor that has a hollow tube bonded to the end face of an optical fiber, and a diaphragm bonded to the hollow tube.

G. Wissmeyer et al., "All-optical optoacoustic microscope based on wideband pulse interferometry," Optics Letters, Vol. 41, Issue 9, pp. 1953-1956 (2016) discloses an all-optical optoacoustic microscope based on a $\pi$-phase-shifted fiber Bragg grating ($\pi$-FBG) with coherence-restored pulsed interferometry (CRPI) used as the interrogation method.

A. Rosenthal et al., "Embedded ultrasound sensor in a silicon-on-insulator photonic platform," Appl. Phys. Lett. 104, 021116 (2014) discloses a miniaturized ultrasound sensor that is based on a $\pi$-phase-shifted fiber Bragg grating formed by waveguide corrugation.

A. Rosenthal et al., "Sensitive interferometric detection of ultrasound for minimally invasive clinical imaging applications," Laser Photonics Rev., Vol. 8, No. 3, pp. 450-457 (2014) discloses miniaturized optical detectors.

C. Zhang el al., "Review of Imprinted Polymer Microrings as Ultrasound Detectors: Design, Fabrication, and Characterization," IEEE SENSORS JOURNAL, Vol. 15, No. 6 (June 2015) discloses ultrasound detectors suitable for photoacoustic imaging.

R. Nuster et al., "Photoacoustic section imaging using an elliptical acoustic mirror and optical detection," JBO Letter, Vol. 17(3), 030503 (March 2012) discloses a method that combines an optical interferometer with an acoustic mirror.

US 2002/0166955 A1 discloses an ultrasonic receiving apparatus including an ultrasonic detecting element for modulating light.

U.S. Pat. No. 7,292,755 B discloses a planar optical waveguide having at least two reflectors.

US 2014/0180030 A1 discloses an intravascular blood pressure and velocity wire.

While the sensors disclosed in these documents provide various benefits over conventional sensors that are based, e.g., on piezoelectric detectors, there is still a need for waveguides and sensors that allow sensing to be performed with good sensitivity, while affording a small cross-section and that, due to their miniaturization, increase the detection bandwidth and angle.

SUMMARY

There is a need in the art for devices and methods that exhibit improved characteristics suitable for sensing or other applications. There is in particular a need for devices and methods that lend themselves to versatile use in sensing or other applications, while affording high sensitivity and having small dimensions. There is in particular a need for such devices and methods that mitigate problems conventionally associated with electromagnetic interference.

According to some embodiments of the invention, there is provided a waveguide having an optical resonator that is monolithically integrated in the waveguide. The optical resonator is defined between a Bragg grating (BG) on one side and at least one reflector on the other side, the at least one reflector having a configuration different from that of the BG. The optical resonator is positioned at an end of the waveguide. The reflector may comprise a reflective layer coated onto an end face (facet) of the waveguide and/or may comprise a material that is susceptible to the induction of surface plasmons at the facet of the waveguide, such as nanoparticles, thereby defining an optical cavity with a high Q factor at an end of the waveguide. The reflector may comprise a further, shorter Bragg grating positioned adjacent the end face of the waveguide. The further, shorter Bragg grating may be interposed between an inner portion of the optical resonator and the end face of the waveguide that may be coated with a reflective layer. The optical resonator is asymmetric in the sense that it is delimited by the Bragg grating on one side and the at least one reflector having a different configuration on the other side.

In some embodiments, a Fabry-Perot-like optical resonator, i.e., an etalon, may be delimited by the Bragg grating and an optically reflective layer, with the Bragg grating and the resonator being part of the waveguide. The reflective layer may be formed at the end of a waveguide, on its end face.

The optical resonator may comprise the Bragg grating and the at least one reflector, with an inner portion of the optical resonator (which can be defined as the portion of the optical resonator interposed between the end of the Bragg grating that is closest to the end face of the waveguide and the part of the at least one reflector that is closest to the Bragg grating) being monolithically formed with the waveguide.

Such a waveguide with integrated optical resonator has various applications. For illustration, acoustic waves, such as ultrasound, incident on the facet can be detected, in contrast to other resonator based sensors. When the waveguide facet, rather than the outer circumferential surface, is used for sensing, the effective sensing size is drastically reduced and the detection bandwidth is increased. Implementation of the optical resonator as part of the waveguide drastically reduces losses and increase light confinement, resulting in a compact sensing device. The asymmetric design allows for maximum exposure of the optical resonator to a stimulus that is to be sensed, as well as an optical read-out of the optical resonator that is essentially free of losses. Sensing performed using the waveguide with integrated optical resonator is immune to electromagnetic interference.

A sensor according to an aspect of the invention comprises a waveguide having a longitudinal axis and an end face, the waveguide comprising a Bragg grating. At least one reflector is provided on the end face of the waveguide. An optical resonator is formed by the Bragg grating, the at least one reflector, and an inner portion of the optical resonator that is located between the Bragg grating and the at least one reflector. The inner portion of the optical resonator extends within a portion of the waveguide. The sensor comprises a detector configured to detect at least one spectral characteristic of the optical resonator or a change of at least one spectral characteristic of the optical resonator.

The at least one spectral characteristic or change of at least one spectral characteristic may comprise any one, or any combination of: at least one resonance frequency of the optical resonator; a shift of at least one resonance frequency of the optical resonator; an intensity of detected light in response to interrogating light measured using coherent continuous wave (cw) interferometry or incoherent cw interferometry; a spectral response of the optical resonator, which may be detected using broadband interrogation; and/or a bandwidth of at least one resonance peak of the optical resonator.

The sensor may be an acoustic sensor, a pressure sensor or a temperature sensor.

The optical resonator may be configured to confine electromagnetic radiation in proximity to the end face, optionally within an end portion of the waveguide that extends between 100 nm and 1 cm, preferably between 200 nm and 5 mm, from the end face. The end portion between the end of the Bragg grating that faces the end face and the end face may preferably have a length of less than 10 mm, more preferably of less than 1 mm, more preferably of less than 100 μm, more preferably of less than 1 μm, more preferably less than 500 nm.

The length of the inner portion of the optical resonator may be measured using, e.g., microscopy, such as white light microscopy, or electron microscopy.

The length of the inner portion of the optical resonator, the length of the Bragg grating, and/or the overall length of the optical resonator may be deduced using computational techniques. For illustration, the overall length of the optical resonator may be determined using spectrum simulations performed by a transfer-matrix method. The spectrum simulations may be compared to measured spectral characteristics.

The sensor may further comprise a source configured to supply electromagnetic radiation to the optical resonator through the Bragg grating. The detector may be configured to detect electromagnetic radiation passing from the optical resonator through the Bragg grating and propagating along the waveguide.

The detector may be configured to sense a spectral response of the optical resonator and/or an intensity of electromagnetic radiation from the optical resonator as a function of time.

The detector may be configured to sense a change in spectral response or change in intensity of light coupled out of the optical resonator as a function of time.

The detector may be configured to sense the change in spectral response or change in intensity triggered by at least one of: a change in distance between the Bragg grating and the at least one reflector; a change in refractive index in the portion of the waveguide; a change in reflectivity of the Bragg grating.

The at least one reflector may comprise at least one reflective layer. The at least one reflective layer may comprise at least one metallic layer and/or at least one dielectric layer.

The at least one reflective layer may be coated directly onto the end face of the waveguide or onto a carrier different from the waveguide.

The at least one reflector may comprise particles or a material configured such that surface plasmons are generated therein to form the optical resonator with the Bragg grating.

The at least one spectral characteristic may be at least one resonance frequency of the optical resonator that may be shifted in response to interaction of a specimen with the surface plasmons in the particles or material.

The at least one reflector may comprise a functionalized surface or a structured metallic layer.

The sensor may comprise an acoustic coupling element attached to the end face of the waveguide. The acoustic coupling element may have a length chosen to match a central frequency of an acoustic wave that is to be sensed.

The sensor may further comprise an acoustic mirror and a retaining mechanism for positioning the optical resonator relative to the acoustic mirror.

The acoustic mirror may comprise a surface that defines at least a portion of a rotational ellipsoid, wherein a major axis of the rotational ellipsoid is tilted with respect to a planar face surface of the acoustic mirror, and wherein the surface that defines at least a portion of the rotational ellipsoid is recessed from the planar face surface.

The retaining mechanism may be configured to position the waveguide such that the waveguide overlaps a focal point of the rotational ellipsoid or is located in proximity to the focal point of the rotational ellipsoid.

The focal point may be located within a cavity of the acoustic mirror.

A sensor array according to an embodiment comprises a plurality of sensors according to any one of the preceding claims. The plurality of sensors may be arranged in a one-dimensional array or in a two-dimensional array.

The sensor array may be used as an acoustic, pressure, or ultrasound imaging device or camera, respectively. Time-divided or simultaneous read-out of the plural sensors may be performed. A size of the sensor array or imaging device may be adapted to a size of the specimen on which imaging is to be performed.

The imaging device or camera may be operative to detect acoustic waves, pressure variations, or ultrasound in a spatially resolved way.

A sensing method according to an aspect of the invention comprises positioning a sensor relative to a specimen. The sensor comprises a waveguide having a longitudinal axis and an end face, the waveguide comprising a Bragg grating, at least one reflector being provided on the end face of the waveguide, and an optical resonator being formed by the Bragg grating, the at least one reflector, and an inner portion of the optical resonator that is located between the Bragg grating and the at least one reflector. The inner portion of the optical resonator extends within a portion of the waveguide. The method comprises detecting at least one spectral characteristic of the optical resonator or a change of at least one spectral characteristic of the optical resonator.

The detected at least one spectral characteristic of the optical resonator or change of at least one spectral characteristic of the optical resonator may be used to perform at least one of the following: acoustic sensing; medical sensing; bio sensing; temperature sensing; frequency differentiation imaging; projection imaging; optoacoustic imaging; optoacoustic non-destructive testing; chemical sensing; plasmonic sensing.

The sensor may be the sensor of any one of the embodiments disclosed herein.

A waveguide with integrated optical resonator according to another aspect of the invention is provided. The waveguide has a longitudinal axis and an end face. The waveguide with integrated optical resonator comprises a Bragg grating in the waveguide and at least one reflector on the end face of the waveguide, wherein an inner portion of the optical resonator between the Bragg grating and the least one reflector extends within a portion of the waveguide.

A sensor according to another aspect of the invention comprises an acoustic transducer, an acoustic mirror, and a retaining mechanism for positioning the acoustic transducer relative to the acoustic mirror.

Various effects are attained by the devices, methods, and assemblies according to embodiments. For illustration, the sensors and waveguides with integrated optical resonator according to embodiments are capable of sensing acoustic waves, other pressure variations, temperature, or other stimuli using the end face, i.e., facet of the waveguide, which has characteristic dimensions that are much smaller than the length of the waveguide. This provides large bandwidth and/or allows plural sensors to be readily combined in a one- or two-dimensional array. When a reflector is provided on an end face of the waveguide, a high Q optical resonator may be formed adjacent the end of the fiber. Read-out can be performed in a mode with both incident light coupled into the optical resonator and outgoing light coupled out of the optical resonator travelling along the same path of the waveguide in opposite directions.

The devices, methods, and assemblies according to embodiments may be used for sensing acoustic waves, other pressure variations, temperature, or other stimuli, without being limited thereto. The devices, methods, and assemblies according to embodiments may be used for acoustic sensing, medical sensing, bio sensing, temperature sensing, frequency differentiation imaging, projection imaging, optoacoustic imaging, optoacoustic non-destructive testing, chemical sensing, or plasmonic sensing, without being limited thereto.

BRIEF DESCRIPTION OF THE DRAWINGS

Embodiments of the invention will be described with reference to the drawings, in which identical or similar reference signs designate identical or similar elements.

DETAILED DESCRIPTION OF EMBODIMENTS

Exemplary embodiments of the invention will be described with reference to the drawings in which identical or similar reference signs designate identical or similar elements. While some embodiments will be described in the context of exemplary fields of use, such as sensing of acoustic waves, in particular ultrasound, and exemplary constructions, such as optical fibers and photonic integrated circuits constructed using a silicon-on-insulator technique, the embodiments are not limited thereto. The features of embodiments may be combined with each other, unless specifically noted otherwise.

The term "optoacoustic" is used herein, it being understood that "photoacoustic" is another synonymous term conventionally used in the art.

As used herein, sensors and waveguides responsive to "acoustic waves" may in particular be responsive to ultrasound waves.

Figure 1:
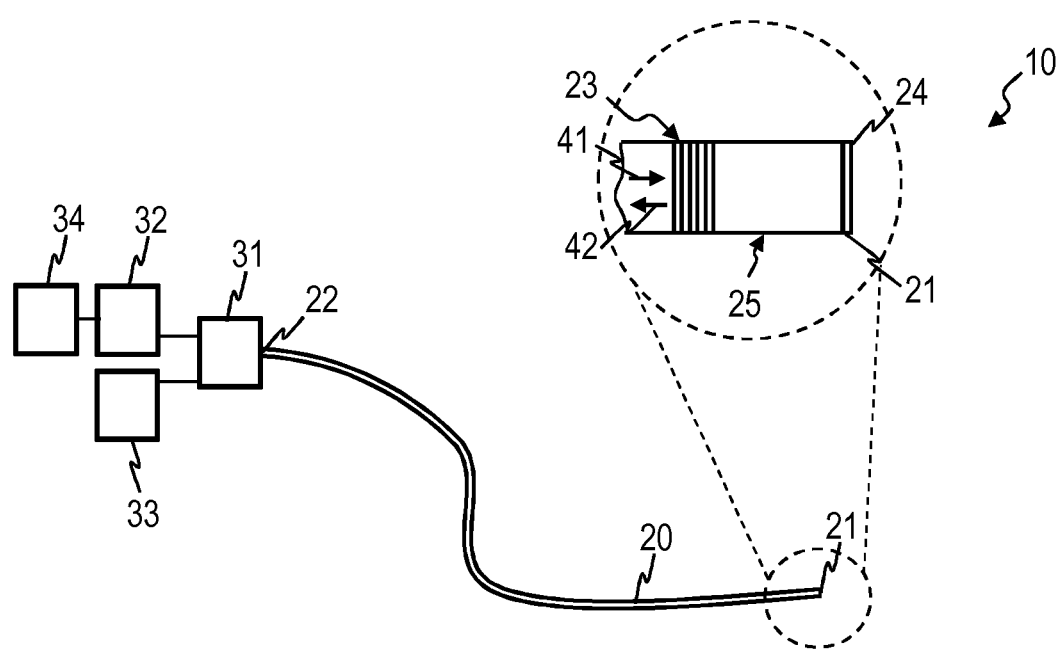
FIG. 1 is a schematic view of a sensor according to an embodiment.

FIG. 1 discloses a sensor 10 according to an embodiment. The sensor 10 comprises a waveguide 20. The waveguide 20 may be a single mode waveguide, a multimode waveguide, a polarization maintaining waveguide, a non-polarization maintaining waveguide, a mode composite waveguide, a photonic crystal fiber, an optical fiber, or a silicon waveguide, without being limited thereto.

The waveguide 20 extends along a longitudinal axis between a first end, at which the waveguide 20 has an end face 21, and a second end 22. As used herein, the term "end face" refers to a facet or face of the waveguide that extends transverse to the longitudinal axis of the waveguide 20, and which may in particular extend perpendicular to the longitudinal axis of the waveguide 20.

The inset in FIG. 1 schematically shows an end portion of the waveguide 20. The waveguide 20 has a Bragg grating (BG) 23. The Bragg grating 23 is formed in the waveguide 20. The Bragg grating 23 is disposed in proximity to, but spaced from the end face 21 of the waveguide 20. At least one reflector 24 is provided on the end face 21. The at least one reflector may be, or may comprise, a reflective layer coated onto the end face 21. The at least one reflector may be, or may comprise, a material or structure provided on the end face 21 that creates surface plasmons and defines an optical resonance between the at least one reflector and the Bragg grating 23.

As used herein, the term "reflector" generally refers to a material or structure that is capable of reflecting light impinging onto it from the Bragg grating 23 back towards the Bragg grating 23. The reflector is different in construction from the Bragg grating 23.

As used herein, a "reflector on the end face of the waveguide" encompasses reflectors that are arranged externally of the waveguide, e.g., in direct abutment with the end face, without being limited thereto. For illustration, the at least one reflector may optionally include reflective elements that are integrally formed with the waveguide and positioned within the waveguide.

An optical resonator 25 comprises the at least one reflector 24, the Bragg grating 23, and an inner portion of the optical resonator 25 that is located between the at least one reflector 24 and the Bragg grating 23. A light beam entering the optical resonator is confined and will reflect repeatedly from the at least one reflector 24 and the Bragg grating 23. This causes the light beam to interfere with itself inside the optical resonator 25. Such an optical resonator 25 has a characteristic spectral response that includes one or multiple resonances.

The sensor 10 comprises a detector 32 coupled to the second end 22 of the optical fiber by a suitable coupling arrangement 31. The detector 32 may comprise an optical filter and demodulator, for example.

The sensor 10 may comprise a source 33 of electromagnetic radiation, which may be a laser or another suitable light source for generating electromagnetic radiation. The electromagnetic radiation may be light. The light may have a wavelength in at least one, or several of, the visible spectral range, the infrared (IR) spectral range, and the ultraviolet (UV) spectral range. The electromagnetic radiation generated by the source 33 may be coupled into the fiber via the coupling arrangement 31. The coupling arrangement 31 may include a 50/50 coupler, for example.

The source 33 of electromagnetic radiation may be coupled to the waveguide 20 via a further waveguide (not shown). The further waveguide may be different from the waveguide 20 in construction. For illustration, the waveguide 20 may be silicon-on-insulator (SOI) platform waveguide, and the further waveguide that couples the source 33 to the waveguide 20 may be an optical fiber that is connected to the waveguide 20.

Electromagnetic radiation, in particular light 41 (which serves as interrogating light for interrogating the optical resonator), output by the source 33 will travel along the waveguide 20 through the Bragg grating 23 and into the inner portion of the optical resonator 25. The light may be reflected multiple times by the Bragg grating 23 and the reflector 24 before being coupled out of the optical resonator 25 through the Bragg grating 23, back towards the second end 22 of the waveguide 20. The light 42 will automatically leak out of the optical resonator 25, due to the Bragg grating 23 having a reflectivity smaller than 100%.

The detector 32 may detect one or several resonance frequencies or other spectral characteristics or changes of spectral characteristics of the optical resonator 25 based on the light coupled out of the optical resonator 25. Detection of an intensity that is indicative of a shift of one or several resonance frequencies may be performed using, e.g., the techniques disclosed in A. Rosenthal et al., Opt. Express Vol. 20, Issue 28, pp. 19016-19029 (2012). Alternatively or additionally to sensing spectral characteristics by sensing an intensity indicative of one or several resonance frequencies of the optical resonator 25 or a shift of the one or several resonance frequencies, other characteristics of the spectral response of the optical resonator 25 may be detected. For illustration, a change in intensity of the light 42 detected at a fixed frequency (e.g., the resonance frequency of the optical resonator when the optical resonator 25 is not exposed to acoustic waves) may be detected.

Coherent continuous wave (cw) interferometry, in which the intensity of interrogating light is split and made to interfere with the light coupled out of the optical resonator 25, or incoherent cw interferometry may be performed.

The detector 32 may e configured to time-sequentially detect one or several resonance frequencies of the optical resonator 25 and/or other spectral characteristics of the optical resonator 25 or changes thereof. For illustration, time-dependent variations in a resonance frequency and/or in other spectral characteristics of the optical resonator 25 may be detected.

A computing device 34 may use the time-dependent variations in a resonance frequency and/or in other spectral characteristics of the optical resonator 25 to determine, e.g., a time-dependent pressure variation, a time-dependent temperature variation, a frequency and/or an intensity of an acoustic wave impinging onto the optical resonator 25, or other quantities.

In one exemplary implementation, the spectral characteristic of the optical resonator or changes in spectral characteristic may be the measured intensity detected at the detector 32 when a continuous wave (cw) interferometry is performed. In this case, the source 33 may be a cw laser. The coupling arrangement 31 may be a circulator/50-50 coupler. The detector 32 may comprise a photodiode. The interference between a portion of light branched off from the output of the source 33 may be made to interfere with the light leaking out of the optical resonator through the Bragg grating 23, and the resultant intensity may be detected by the photodiode. The readout of the photodiode may be performed by a data acquisition system of a computer 34, but may also be implemented in other ways without requiring use of a computer. The cw laser may be controlled by a computer, but may also be controlled using other mechanisms.

The cw interferometry may be implemented as coherent cw interferometry or as incoherent cw interferometry.

In coherent cw interferometry, the cw laser is tuned to a resonance frequency of the optical resonator or to a value within the full-width-half-max (FWHM) of the resonance frequency. A perturbation to the resonator, which may be caused by ultrasound or a temperature shift, shifts the resonance condition of the resonator. Hence, a change in the intensity at the read-out photodiode can be detected.

In incoherent cw interferometry, a broadband light source 31 interrogates the resonator and assumes the spectral shape of the resonator. Perturbations or temperature changes will shift the resonance condition and resulting shifts in the mean wavelength of this spectral shape can then be monitored (i.e., demodulated) with at least one of a wavelength-meter, a spectrometer or a Mach-Zehnder interferometer. Broadband pulsed interferometry of broadband light sources in combinations with wavelength-meters or spectrometers may be employed for interrogating or reading out the optical resonator 25.

The optical resonator 25 may e configured to confine light within a portion of the waveguide that extends over a length from the end face 21, with the length being from 100 nm to 1 cm, preferably from 200 nm to 5 mm. An end portion between the end of the Bragg grating 23 that faces the end face 21 and the end face 21 may preferably have a length of less than 10 mm, more preferably of less than 1 mm, more preferably of less than 100 µm, more preferably of less than 1 µm, more preferably less than 500 nm.

The Bragg grating 23 may have a reflectivity that may preferably be at least 90%, even more preferably at least 95%, even more preferably at least 97%. The at least one reflector 24 may have a reflectivity that may preferably be at least 90%, even more preferably at least 95%, even more preferably at least 96%, even more preferably at least 98%, even more preferably at least 99%.

FIG. 2 to FIG. 5 respectively show various variants of the waveguide 20 that may be used in the sensor 10.

Figure 2:
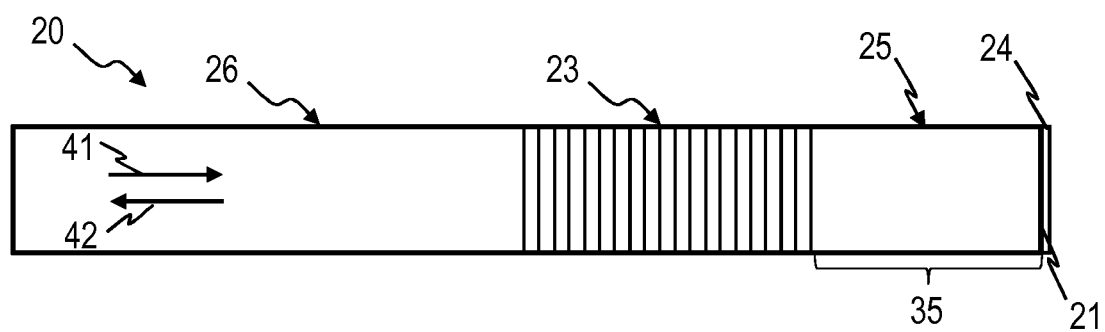
FIG. 2 is a schematic view of a waveguide with integrated optical resonator according to an embodiment.

FIG. 2 is a schematic view of a waveguide 20 comprising a Bragg grating 23 and at least one reflector 24 on an end face 21 of the waveguide 20. An optical resonator 25 is formed by the Bragg grating 23, the at least one reflector 24, and an inner portion of the optical resonator 25 that extends between the Bragg grating 23 and the at least one reflector 24. The inner portion of the optical resonator 25 is integrated into the waveguide 20. The at least one reflector 24 may be a reflective coating, for example. The inner portion of the optical resonator 25 may have a length 35 that is defined between the end face 21 of the waveguide 20 and the end of the Bragg grating 23 that is closest to the end face 21. The inner portion of the optical resonator 25, which is interposed between the end of the Bragg grating 23 that is closest to the end face 21 and the surface of the reflector(s) 24 closest to the Bragg grating 23, may have a length $L_C$ 35 that is shorter or longer than a length of the Bragg grating 23. This inner portion of the optical resonator 25, located in between the Bragg grating and the reflector(s) 24 that are disposed adjacent the end face 21, is also referred to as inner portion of the optical resonator herein. While the inner portion of the optical resonator 25 is similar in function to the cavity defined between two mirrors in a conventional Fabry-Perot resonator, in embodiments of the invention the inner portion of the optical resonator 25 is a part of the waveguide 20 that is located in proximity to the end face 21.

The optical resonator 25 has an asymmetric construction, being delimited by different reflective elements 23, 24 on opposing sides. The optical resonator 25 is positioned in proximity to a first end of the waveguide 20. A long portion 26 of the waveguide 20 is connected to the optical resonator 25 only via the Bragg grating 23, while no portion of the waveguide 20 extends from the opposite side of the optical resonator 25 beyond the end face 21.

The waveguide 20 may be an optical waveguide. In this case, the optical resonator 25 is part of the optical waveguide 20 and is located close to the physical end of the waveguide 20.

The optical resonator 25 is delimited on one side by the Bragg grating 23 and, in the embodiment of FIG. 2, on the other side by a reflective layer on the end face 21 of the waveguide 20. Light 41 is guided into the optical resonator 25 from the portion 26 of the waveguide trough the Bragg grating 23. The optical resonator 25 is realized monolithically inside the waveguide 20. The optical readout of the optical resonator 25 can be performed in a lossless manner through the Bragg grating 23. This principle takes advantage of the high spatial light confinement that the Bragg grating 23 enables, and leads to a compact and sensitive optical resonator 25 at the tip of the waveguide 20. Together with a high Q-factor, a high sensitivity in sensing applications may be attained.

Any physical changes to the optical resonator 25, such as compression of the optical resonator 25, pressure or temperature induced changes on the periodicity of the Bragg grating 23 and/or of the reflective coating layer 24 will result in variations of the reflected spectrum and can be monitored.

The purely optical nature of the sensor that includes the waveguide 20 with integrated optical resonator 25 makes it immune to electromagnetic interference. If realized in a low loss waveguide, e.g. a single mode fiber used for telecommunication in optical networks, the optical resonator 25 can be positioned many kilometers away from its read-out setup, e.g., the detector 32, without hindering its performance.

Figure 3:
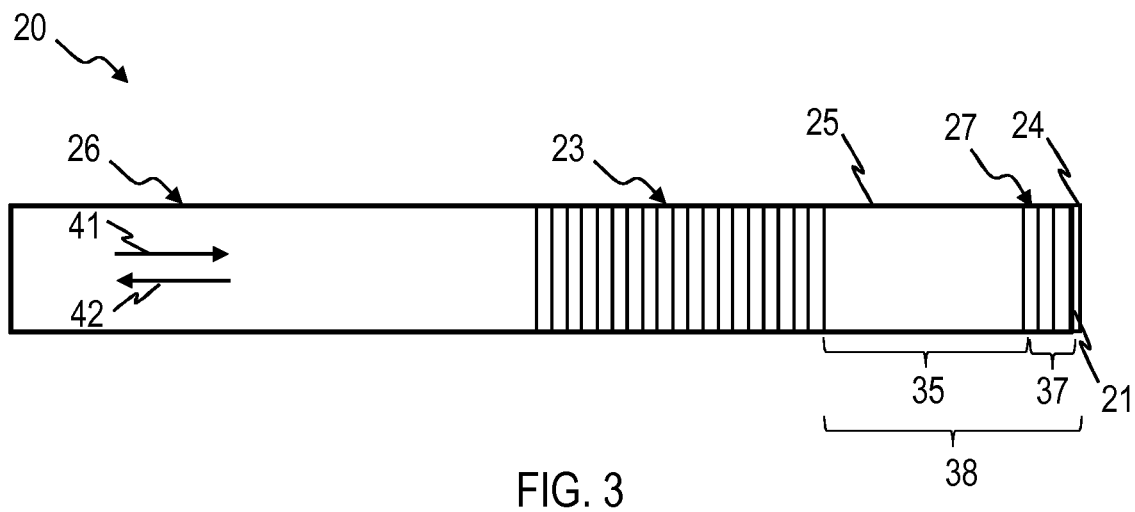
FIG. 3 is a schematic view of a waveguide with integrated optical resonator according to an embodiment.

FIG. 3 is a schematic view of a waveguide 20 comprising a Bragg grating 23 and at least one reflector 24 on an end face 21 of the waveguide 20. An optical resonator 25 is formed by the Bragg grating 23, the at least one reflector 24, 27, and an inner portion of the optical resonator 25 that extends between the Bragg grating 23 and the at least one reflector 24. The inner portion of the optical resonator 25 is integrated into the waveguide 20. One or several optical elements 27 are interposed between the inner portion of the optical resonator 25 and the reflective layer 24 on the end face 21. The one or several optical elements 27 may be formed integrally with the waveguide 20. The one or several optical elements 27 may include alternating regions of different refractive index. The one or several optical elements 27 may include a further Bragg grating that is much shorter than the Bragg grating 23. The one or several optical elements 27 may be reflective elements that assist in keeping light inside the inner portion of the optical resonator 25, aiding operation of the reflective layer 24. The at least one reflector may comprise the further Bragg grating or other reflective elements 27, disposed adjacent the end face of the waveguide in the interior of the waveguide.

The inner portion of the optical resonator 25 may have a length $L_C$ 35 that is shorter or longer than a length of the Bragg grating 23. The one or several optical elements 27 may extend over a distance $L_R$ 37 from the end face 21 into the interior of the waveguide 20. The length $L_C$ 35 of the inner portion of the optical resonator 25 may be defined between the one of the optical elements 27 that faces the Bragg grating 23 and the end of the Bragg grating 23 that faces towards the optical elements 27.

Figure 4:
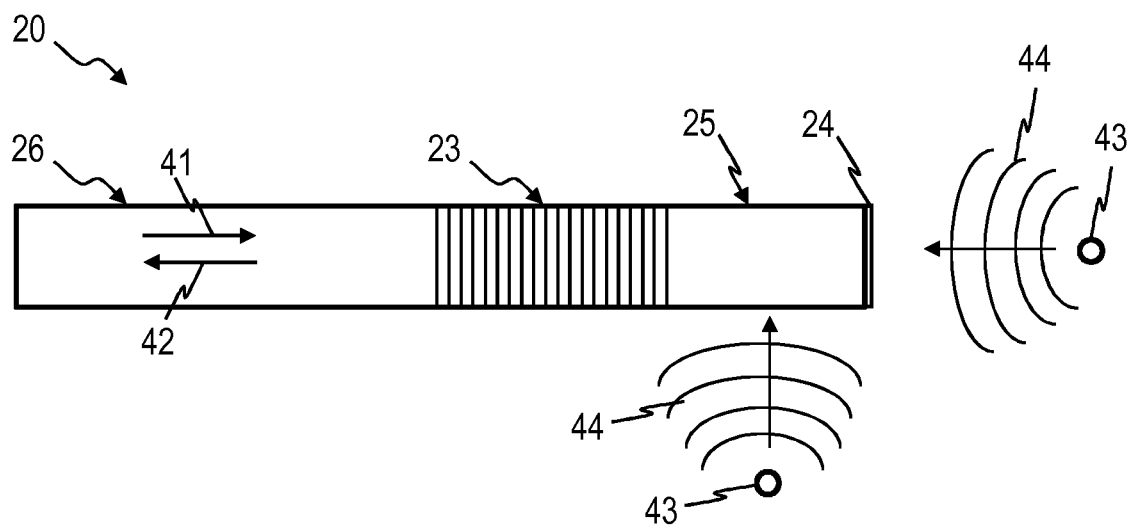
FIG. 4 is a schematic view of a waveguide with integrated optical resonator according to an embodiment.

FIG. 4 is a schematic view illustrating the waveguide 20 with integrated optical resonator 25 in one exemplary use case. The optical resonator 25 is positioned in proximity to an acoustic source 43 that may emit acoustic waves 44. The acoustic waves 44 may be ultrasound waves. Impingement onto the optical resonator 25 causes the optical resonator 25 to compress and/or causes pressure induced changes on the periodicity of the Bragg grating 23 and/or of the reflective coating layer 24. The resultant variations of the reflected spectrum, i.e., of the resonance frequencies as detected in the return light 42, can be monitored.

Figure 5:
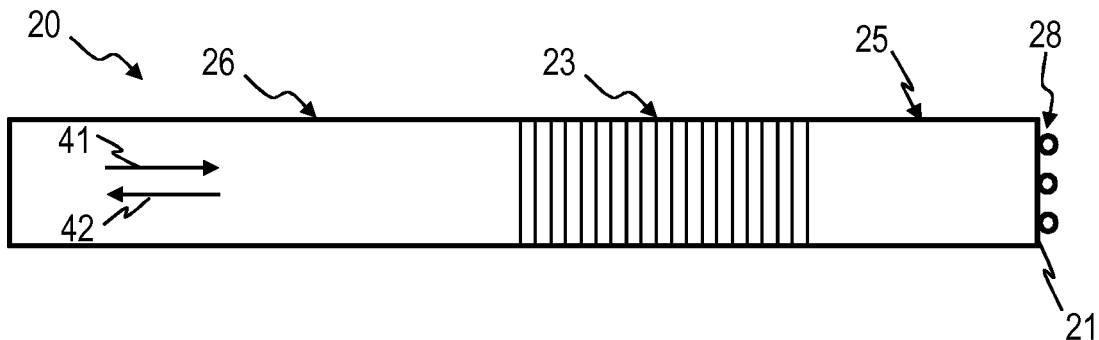
FIG. 5 is a schematic view of a waveguide with integrated optical resonator according to an embodiment.

FIG. 5 is a schematic view of a waveguide 20 comprising a Bragg grating 23. Metallic nanoparticles 28 or any other material or structure capable of surface plasmon excitation are provided on the end face 21. An optical resonator 25 comprises the Bragg grating 23, the metallic nanoparticles 28, and an inner portion of the optical resonator between the Bragg grating 23 and the metallic nanoparticles. The inner portion of the optical resonator is integrated into the waveguide 20. Surface plasmons are created in the metallic nanoparticles 28 or other material or structure capable of surface plasmon excitation, to provide an optical resonance between them and the Bragg grating 23. The optical resonator 25 as illustrated in FIG. 5 may be particularly suitable for use as a biosensor or as a chemical sensor.

It will be appreciated that the reflector 28 may allow an electromagnetic field to be generated beyond the end face 21 of the waveguide 20. Light in the optical resonator 25 can create surface plasmons in the nanoparticles 28 on the end face 21. In turn, the electromagnetic field of the surface plasmons can then extend into a specimen, such as a biological sample. For good sensing accuracy, it is desirable to trap light in close proximity to the end face 21, such as within less than 500 nm, preferably less than 200 nm, more preferably about or less than 100 nm from the end face 21 in the optical resonator. An end portion between the end of the Bragg grating 23 that faces the end face 21 and the end face 21 may preferably have a length of less than 10 mm, more preferably of less than 1 mm, more preferably of less than 100 μm, more preferably of less than 1 μm, more preferably less than 500 nm. This allows sensing to be performed on structures and/or features that do not emit stimuli that physically impinge on the optical resonator 25. For illustration, structures and/or features located within tissue at a depth may be sensed using the waveguide 20.

When the surface plasmons interact with a specimen, such as a biological specimen or a test specimen for non-destructive testing, the resonance frequency or resonance frequencies of the optical resonator 25 are shifted.

In any one of the embodiments, the optical waveguide 20 can be single mode (SM) or multimode, polarization maintaining (PM) or non-PM waveguide and can be manufactured from a wide range of materials, such as polymers, silicon and silica. The geometry of the waveguide 20 can vary as well. The waveguide 20 can have various cross sections, including rectangular, ellipsoidal and circular geometries.

The reflective layer 24, 28 can be realized in a number of different methods, including reflective metallic or dielectric layers 24. These can be applied, e.g., by deposition, by gluing via an intermediate layer, by doping of the waveguide or by growing crystalline structures.

The Bragg grating 23 can be manufactured via UV inscription, laser interference methods, or by any other means such as stacking of dielectric slabs. The index profile of the Bragg grating 23 can be of a variety of shapes, such as rectangular, sinusoidal, apodized, superstructure or a combination of the above. Other parameters, such as the periodicity, duty cycle, and the coupling coefficient can vary as well. The periodicity of the Bragg grating 23 can be matched to the length of the inner portion of the optical resonator 25 to ensure that the Bragg grating 23 exhibits high reflectivity at a wavelength that is chosen such that light having this wavelength acquires a phase shift that is approximately $\pi$ or approximately an integer multiple of $\pi$ upon one passage through the length of the inner portion of the optical cavity (i.e., from leaving the Bragg grating 23 to impinging onto the at least one reflector 24, 28) and/or such that a total round trip phase shift in the inner portion of the optical resonator (i.e., from leaving the Bragg grating 23 to impinging onto the Bragg grating 23 again) is approximately $\pi$ or approximately an odd integer multiple of $\pi$ (i.e., $\pi$, 3 $\pi$, 5 $\pi$, 7 $\pi$, etc.).

In the waveguides with integrated optical resonator explained above, the optical resonator 25 may in particular be a Fabry-Perot-resonator (or etalon) manufactured inside an optical waveguide 20, which is confined by a reflective layer 24 on the one side and a Bragg grating 34 on the other side. The read-out of the optical resonator 25 is performed through the Bragg grating 23 in a virtually loss-free manner.

In the waveguides with integrated optical resonator, the optical resonator 25 has a sensing length that is smaller than the overall length of the optical resonator.

A detector or sensing length may be the sum of a length of the reflector at the end facet and a length within the optical waveguide that includes the inner portion of the optical resonator. The length within the optical waveguide that includes the inner portion of the optical resonator may exceed the length $L_C$ 35 of the inner portion of the optical resonator.

The overall length of the optical resonator may additionally include the full length of the Bragg grating that delimits the optical resonator within the waveguide.

The sensing length may be set to be smaller than the overall length of the optical resonator. This allows the sensing length to be decoupled from the respective acoustic wavelength of the measured acoustic (e.g., ultrasound) signals, providing a broad bandwidth/frequency response towards acoustic signals.

The specific numerical values for the sensing length and/or the overall detector length may depend on the implementation of the waveguide and optical resonator (e.g., optical fiber or silicon-on-insulator technology). The specific numerical values for the sensing length and/or the overall detector length may depend on the sensing application for which the sensor is designed. For illustration, the sensing length may be not more than 100 μm, not more than 50 μm, not more than 10 μm, or not more than 1 μm. The overall detector length may be larger, e.g., not more than 1 cm, not more than 0.5 cm, not more than 0.1 cm, or not more than 200 μm.

The waveguide may be an optical fiber. In this case, the sensing length may be not more than 100 μm and the overall detector length may be not more than 1 cm; or the sensing length may be not more than 50 μm and the overall detector length may be not more than 0.5 cm; or the sensing length may be not more than 10 μm and the overall detector length may be not more than 0.1 cm.

The waveguide may be a polymeric waveguide. In this case, the sensing length may be not more than 100 μm and the overall detector length may be not more than 1 cm; or the sensing length may be not more than 50 μm and the overall detector length may be not more than 0.5 cm; or the sensing length may be not more than 10 μm and the overall detector length may be not more than 0.1 cm.

The waveguide may be a silicon-on-insulator (SoI) waveguide. In this case, the sensing length may be not more than 1 μm and the overall detector length may be not more than 1 mm; or the sensing length may be not more than 10 μm and the overall detector length may be not more than 200 μm; or the sensing length may be not more than 1 μm and the overall detector length may be not more than 200 μm.

While waveguides with integrated optical resonator have been explained above in the context of sensing applications, the waveguides with integrated optical resonator may be used in a wide variety of other applications in which light confinement close to the tip of a waveguide is desired. For illustration, the waveguides with integrated optical resonator may be used in applications in which no interrogation with light 41 is performed.

FIG. 6 to FIG. 9 are schematic views of waveguides with integrated optical resonator that have been manufactured and with which a number of experiments have been conducted.

Figure 6:
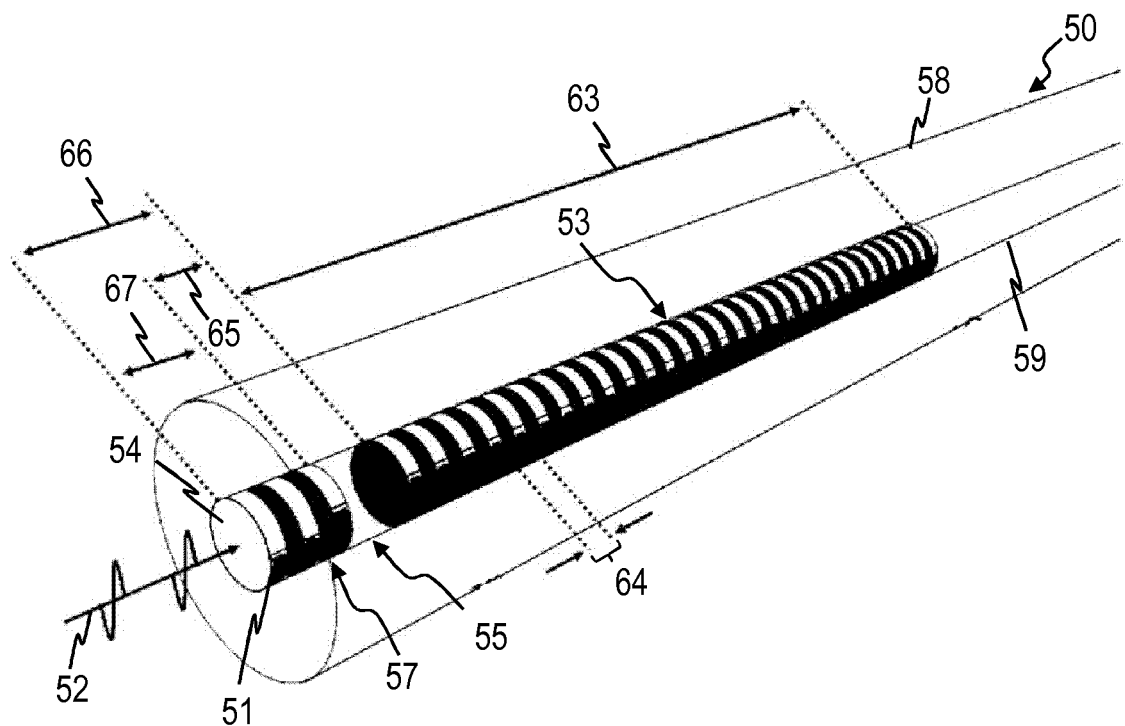
FIG. 6 is a schematic perspective view of a waveguide with integrated optical resonator according to an embodiment.
Figure 7:
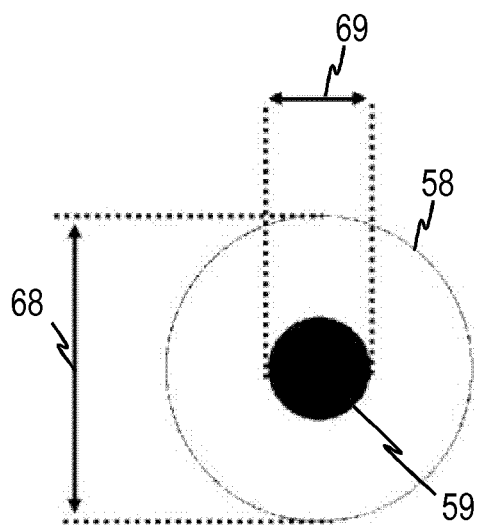
FIG. 7 is a plan view of an end face of the waveguide with integrated optical resonator of FIG. 6, in a viewing direction along a longitudinal direction of the waveguide.

FIG. 6 is a schematic perspective view of a waveguide 50 with integrated optical resonator 55. FIG. 7 is a plan view onto an end face 51 of the waveguide 50.

The waveguide 50 is an optical fiber having a fiber core 59 and a fiber cladding 58. The optical fiber extends along a longitudinal axis and has an end face 51, also referred to as facet, which may extend transverse, and in particular perpendicular, to the longitudinal axis. An optically reflective layer 54 is applied onto the end face 51, e.g., by coating or by using any one of the techniques described above.

A fiber Bragg grating 53 is formed in the core 59. Any one of the techniques described above may be used to form the fiber Bragg grating 53.

In addition to the reflective layer 54, additional optical elements 57 may optionally be provided. The additional optical elements 57 may be disposed in the waveguide 50, so as to be interposed between the inner portion of the optical resonator 55 and the optically reflective layer 54. The additional optical elements 57 may be reflective elements, such as a further fiber Bragg grating shorter than the fiber Bragg grating 53. The at least one reflector disposed on the end face may include the optically reflective layer 54 and, optionally, the further fiber Bragg grating.

The fiber Bragg grating 53 has a length $L_B$ 63 along the longitudinal axis of the waveguide 50. The inner portion of the optical resonator 55 has a length $L_C$ 65 along the longitudinal axis of the waveguide 50. The reflective optical elements 57 have a length $L_R$ 67 along the longitudinal axis. The fiber Bragg grating 53 starts at a distance $L_G$ 66 equal to $L_R+L_C$ from the end face 51.

Experiments have been performed for a waveguide 50 that is a single mode (SM) polarization maintaining (PM) 1550 fiber. In the waveguide used for the experiments, the fiber core 59 has a diameter 69 of 10 μm, and the fiber cladding 58 has a diameter 68 of 125 μm. In the waveguide used for the experiments, the Bragg grating 63 has a length $L_B$ of 2 mm, written with a period P of 300 nm into the fiber core by UV inscription. In the waveguide used for the experiments, the inner portion of the optical resonator 55 has a length $L_C$. On the opposite side, a further Bragg grating 57 having a length $L_R$ 67 of approximately 10 μm is written with a period of 300 nm into the fiber core by UV inscription. The reflective layer 54 is a metallic reflective coating (Ti (5 nm) and Au (100 nm)) which is deposited on the end face 54 of the fiber by sputter deposition. The further Bragg grating 57 may assist in reflection and may be a reflector disposed within the waveguide that supports the function of the reflective layer 54 to confine light.

The length $L_C$ may be set such that the interrogating light coupled into the optical resonator acquires a phase shift that is approximately π or an integer multiple of n upon passage through the length Le (i.e., when covering the distance from leaving the Bragg grating 53 to impinging onto the reflective optical element 54, 57 that is disposed closest to the Bragg grating) and/or a total round trip phase shift in the inner portion of the optical resonator is approximately π or an odd integer multiple of π (i.e., approximately π, 3π, 5π, 7π, etc.).

The optical resonator 55 integrated into the optical fiber was tested for detecting ultrasonic signals 52 generated from a wideband optoacoustic point source (200 nm Au layer illuminated by 523 nm pulsed laser (pulse length 1 ns) focused onto a spot of ~3 μm).

Figure 10:
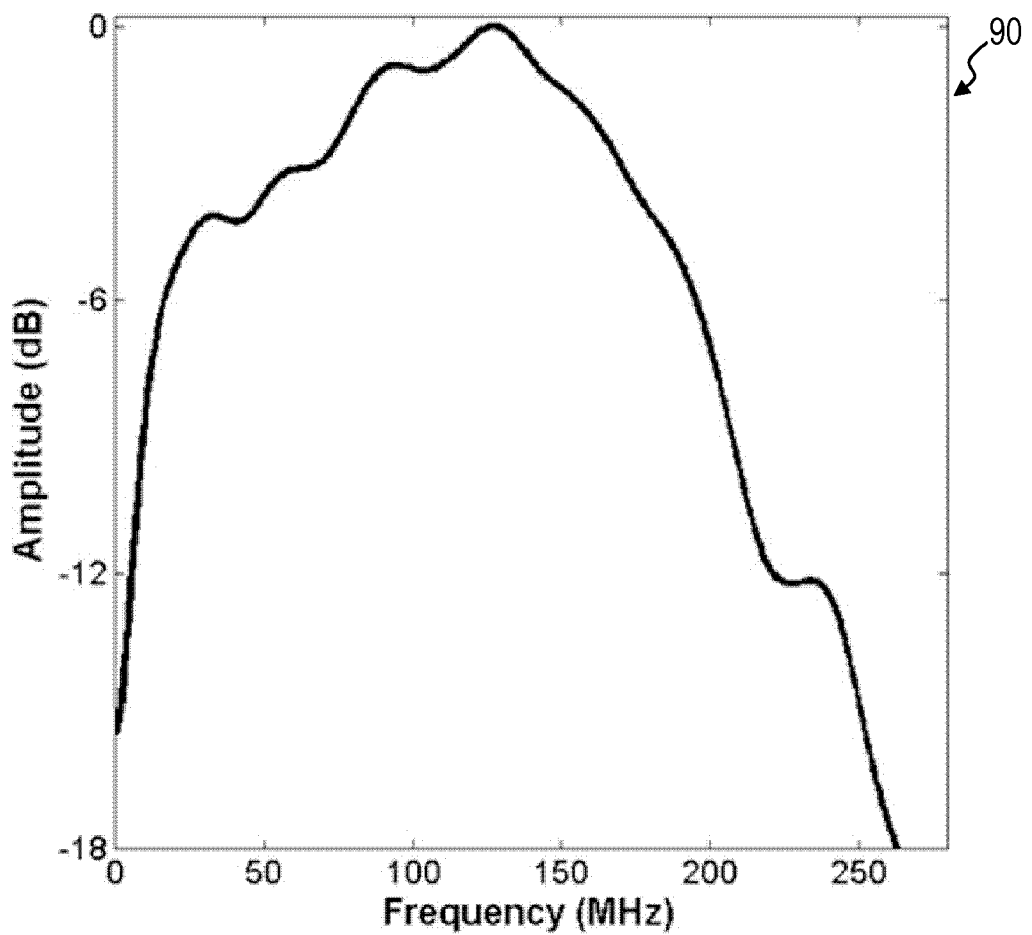
FIG. 10 is a graph representing a frequency response of a waveguide with integrated optical resonator to an acoustic point source as a function of acoustic frequency.

FIG. 10 shows the obtained frequency response of the optical resonator 55 integrated into the waveguide 50, as a function of frequency of acoustic waves generated by an acoustic point source and incident onto the optical resonator 55. A bandwidth of 230 MHz at a central detection frequency of 105 MHz was determined. The graph 90 indicates the change in intensity of light 42 coupled out of the optical resonator 55 through the fiber Bragg grating 53 and detected by the detector coupled to the second end of the waveguide 50, respectively as a function of frequency of acoustic waves incident onto the optical resonator 55. As illustrated, a large detection bandwidth is attained.

The sensitivity of the optical resonator 55 integrated into the waveguide 50 towards ultrasound 52 was determined with the help of a calibrated needle hydrophone and was found to be 30 Pa in terms of noise equivalent pressure over a bandwidth of 25 MHz around the central frequency. Thus, high sensitivity can be attained over a wide bandwidth.

The waveguide 50 with optical resonator 55 is responsive to acoustic waves, such as ultrasound, incident on the end face 51 that has a comparatively small diameter. This allows plural waveguides 50 with optical resonator 55 to be arranged in a one- or two-dimensional sensor array, as will be explained with reference to FIG. 16 below.

Figure 11:
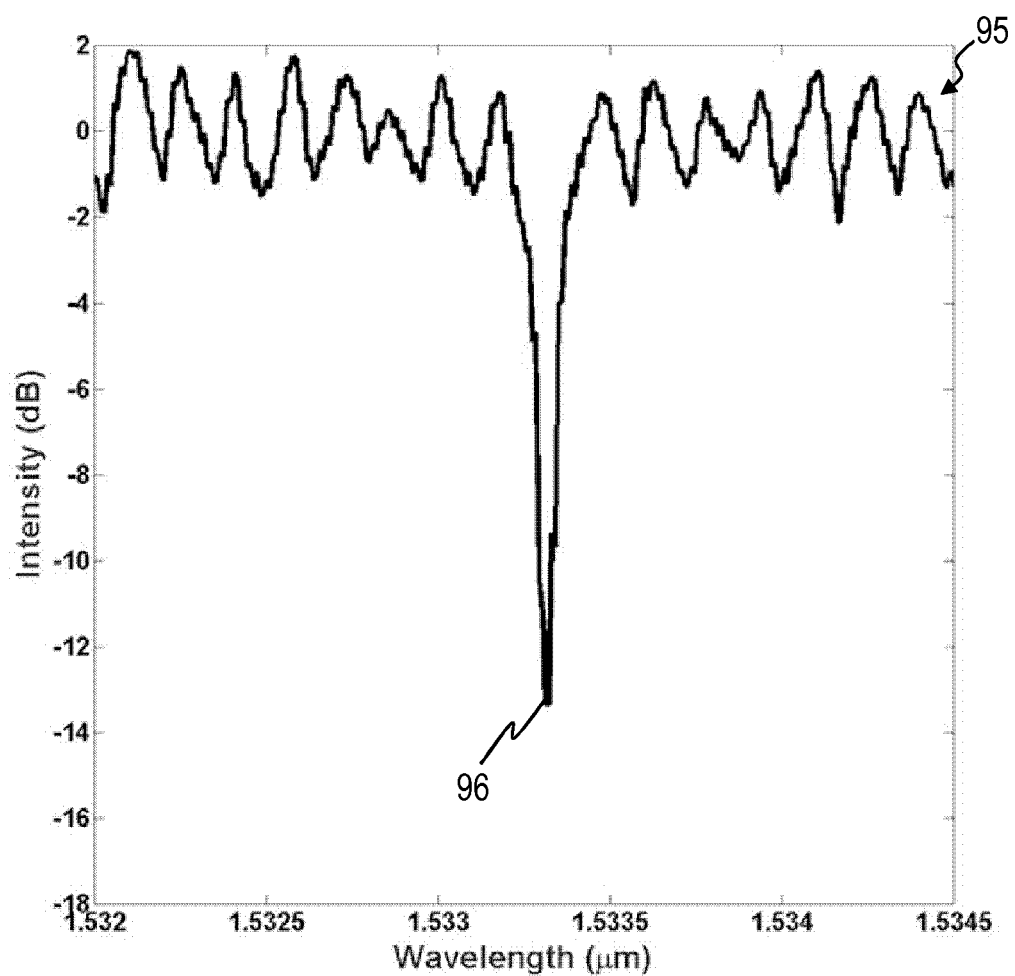
FIG. 11 is a graph representing a resonance spectrum of an optical resonator according to an embodiment, shown with spectral inversion.

FIG. 11 shows the spectrum 95 of the optical resonator 55 integrated into the waveguide 50, as a function of light wavelength. A measurement technique with spectral inversion was used, causing the resonance frequency of the optical resonator to show up as a negative peak in the spectrum. The spectral response has a pronounced peak 96, corresponding to a resonance of the optical resonator 55. The length of the inner portion of the optical resonator 55 and the wavelength of the light generated by the source 31 (see FIG. 1) may be matched. Light having the resonance frequency of the optical resonator acquires a phase shift that is approximately n or approximately an integer multiple of π upon passage through the length $L_C$ (i.e., when covering the distance from the surface of the Bragg grating that is closest to the end face and the surface of the at least one reflector that is disposed closest to the Bragg grating), and/or a total round trip phase shift in the inner portion of the optical resonator may be approximately π or an odd multiple of π (i.e., π, 3 π, 5 σ, 7 π, etc.).

A waveguide 50 as described with reference to FIG. 6 and FIG. 7 may be particularly suitable for use in optoacoustic microscopy, without being limited thereto.

Various other types of waveguides may be used. For illustration, the waveguide with integrated optical resonator may be realized in a in a Silicon-on-Insulator (SOI) platform using standard manufacturing techniques from the microelectronics industry and the silicon photonics field.

Figure 8:
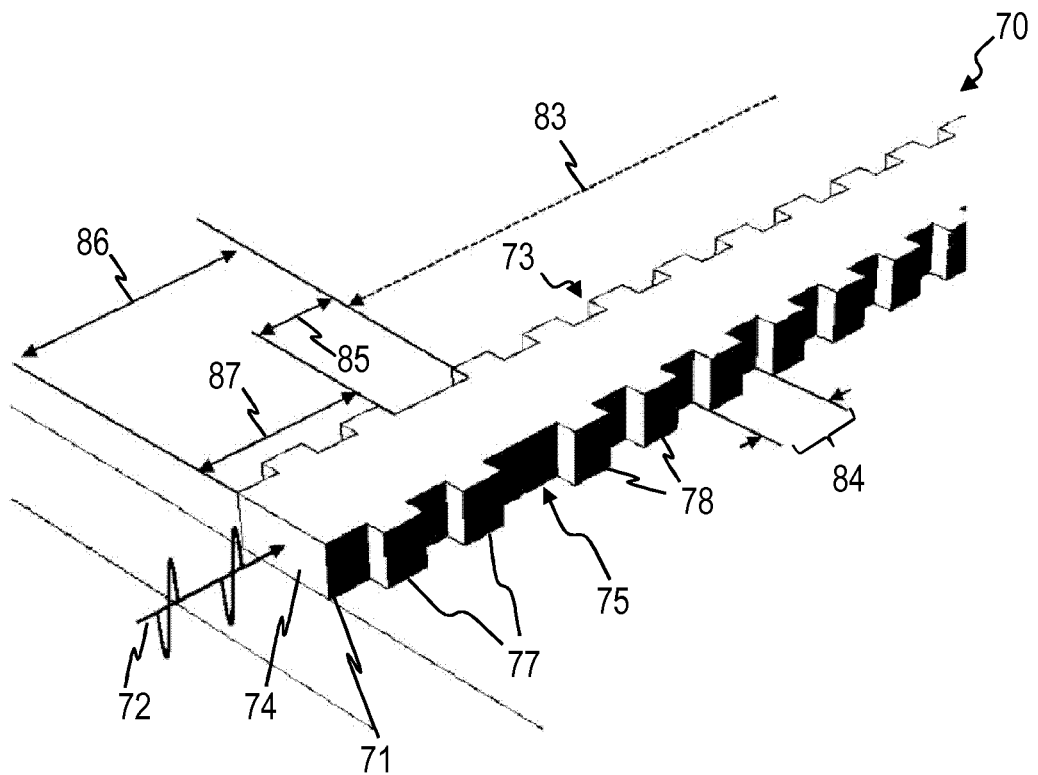
FIG. 8 is a schematic perspective view of a waveguide with integrated optical resonator according to an embodiment.
Figure 9:
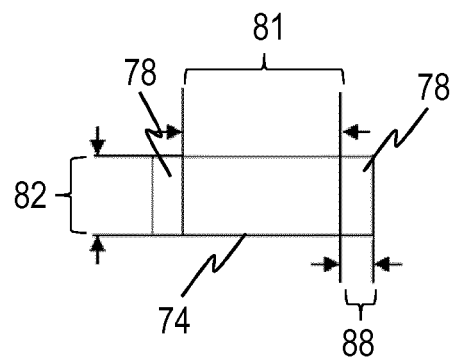
FIG. 9 is a plan view of an end face of the waveguide with integrated optical resonator of FIG. 8, in a viewing direction along a longitudinal direction of the waveguide.

FIG. 8 is a schematic perspective view of a waveguide 70 with integrated optical resonator 75. FIG. 9 is a plan view onto an end face 71 of the waveguide 70.

The waveguide 70 is formed on an SOI wafer. The waveguide 70 may be an integrated photonic circuit. The waveguide 70 extends along a longitudinal axis and has an end face 71, also referred to as facet, which may extend transverse, and in particular perpendicular, to the longitudinal axis. An optically reflective layer 74 is applied onto the end face 71, e.g., by coating or by using any one of the techniques described above.

A fiber Bragg grating 73 is formed in the waveguide 70. The fiber Bragg grating 73 is formed by corrugations 78 on the side walls of the waveguide 70.

In addition to the reflective layer 74, additional optical elements 77 may optionally be provided in the waveguide 70. The additional optical elements 77 may be disposed in the waveguide 70, so a to be interposed between the inner portion of the optical resonator 75 and the optically reflective layer 74. The additional optical elements 77 may be reflective elements, such as a further fiber Bragg grating shorter than the Bragg grating 73, disposed in the waveguide 70.

The fiber Bragg grating 73 has a length $L_B$ 83 along the longitudinal axis of the waveguide 70. The inner portion of the optical resonator 75 has a length $L_C$ 85 along the longitudinal axis of the waveguide 70. The additional optical elements 77 have a length $L_R$ 87 along the longitudinal axis. The Bragg grating 73 starts at a distance $L_G$ 86 equal to $L_R+L_C$ from the end face 71.

Experiments have been performed for a waveguide 70 fabricated on an SOI wafer with a crystalline Si orientation of (100). The optical resonator 75 is formed in a rectangular Si waveguide with a cross-section of 220 nm×500 nm, which is embedded between a buried $SiO_2$ layer of 2 μm thickness and a $SiO_2$ cladding of 1.25 μm thickness. The waveguide is approximately 2 mm long and divided into several sections. One section is the Bragg grating 73, which has a length $L_B$ of 125 μm. The fiber Bragg grating 73 forms one of the optically reflecting surfaces of the optical resonator 75. Periodic variations in the effective refractive index are produced by adding a side corrugation to the Si waveguide with a periodicity 84 of 320 nm and a duty cycle of 50%. The corrugation depth Aw (shown by reference sign 88) is 40 nm.

The next section of the waveguide 70 is the inner portion of the optical resonator 75, which has a length $L_C$. Light at the resonance frequency may acquire a phase shift that is approximately n or an integer multiple of π upon one passage through the inner portion with length $L_C$ (i.e., from leaving the Bragg grating 73 to impinging onto the further Bragg grating 77), and/or a total round trip phase shift in the inner portion with length $L_C$ (i.e., from leaving the Bragg grating 73 to impinging onto the Bragg grating 73 again) may be approximately 7 or an odd integer multiple of π (i.e., π, 3 π, 5 π, 7 π, etc.). The further optical elements 77 form a further fiber Bragg grating 77 approximately 10 μm long, wherein periodic variations in the effective refractive index are produced by adding a side corrugation with a periodicity of 320 nm and a duty cycle of 50%. The intersection of the waveguide and the reflecting surface defines the sensing area.

As the high refractive index contrast in the SOI platform leads to a strong spatial confinement of the optical mode in the waveguide, the sensing area corresponds to the cross-section of the waveguide.

The silicon optical resonator 75 was tested for detecting ultrasonic signals 72 generated from a wideband ultrasonic point source (200 nm Au layer, illuminated by a 523 nm pulsed laser, pulse duration 1 ns, focused onto a spot of 3 μm). The frequency response of the optical resonator 75 was determined to have a bandwidth of 230 MHz, with a central detection frequency of 88 MHz. Thus, a high bandwidth is attained.

The sensitivity of the silicon optical resonator 75 towards ultrasound was determined with the help of a calibrated needle hydrophone and was found to be 60 Pa in terms of noise equivalent pressure over a bandwidth of 25 MHz around the central frequency. Thus, high sensitivity is attained over a wide bandwidth.

In any one of the waveguides with integrated optical resonator 25, 55, 75 described above, the end of the Bragg grating 23, 53, 73 that faces towards the end face 21 is located at a distance from the end face 21 which is $L_G L_C$ if no additional optical elements are interposed between the inner portion of the optical resonator and the end face 21, and which is $L_G=L_C+L_R$ when additional optical elements are interposed between the inner portion of the optical resonator and the end face 21. The distance $L_G$ may be in the range from 100 nm to 1 cm, preferably from 200 nm to 5 mm. The distance $L_G$ may be greater than 100 nm, in particular greater than 200 nm, in particular greater than 500 nm. The distance $L_G$ may be may preferably be less than 10 mm, more preferably less than 1 mm, more preferably less than 100 μm, more preferably less than 1 μm, more preferably less than 500 nm. The optical resonator 25, 55, 75 may confine light within a portion of the waveguide that is located within a range from 100 nm to 1 cm, preferably from 200 nm to 5 mm, from the end face 21 of the waveguide.

The waveguides with optical resonator 25, 55, 75 may respectively be used in such a way that the end face with the reflector is exposed to the stimulus that is to be sensed (which may, e.g., be an acoustic wave, in particular an ultrasound wave, temperature, or other stimuli). This allows several waveguides with optical resonators to be combined into a sensor array that provides high spatial resolution and affords the integration of a large number of sensors per unit area. The waveguides with optical resonator 25, 55, 75 may also be used in such a way that the lateral side surface of the optical resonator 25, 55, 75 and/or Bragg grating 23, 53, 73 is exposed to the stimulus to be sensed.

Sensors comprising the waveguides with optical resonator 25, 55, 75 have a wide variety of applications, some of which are described below:

a. Acoustic Sensing

The optical resonator 25, 55, 75 is very sensitive towards mechanical vibrations. This renders it very suitable as an acoustic detector in various fields, such as biomedical ultrasound and imaging, optoacoustic/photoacoustic imaging and non-destructive testing (NDT) of materials.

b. Medical Sensing Device

The ultra-broad frequency response of the optical resonator 25, 55, 75 allows a wide variety of absorber sizes and their optical absorbance spectra to be measured. In the context of medical sensing, this would enable to monitor and analyze biochemical and biophysical characteristics deep within tissue. Detecting and monitoring the optical absorption spectrum of blood can reveal information about metabolite parameters such as blood oxygenation as well as physical parameters such as density and average vessel diameter of vasculature which in turn is an indicator of cardiovascular health.

c. Bio-Sensing

The design of the optical resonator 25, 55, 75, which is delimited by two different optically reflecting surfaces, creates strong light confinement in close proximity to the end of the respective waveguide. This allows the optical resonator 25, 55, 75 to be used in the field of bio-sensing, where, e.g., changes in the molecular composition and the physical parameters of a specimen can be monitored. For example, surface plasmons (SPs) can be induced when the reflective layer on the end face of the waveguide is either metallic or contains metallic particles. Another variant is to apply a semitransparent or extremely thin reflective layer. In this way the optical mode confined in the waveguide will be exposed to the surroundings and can interact with the examined specimen.

d. Temperature Sensing

The resonance wavelength of the optical resonator 25, 55, 75 depends on the length of the optical resonator as well as on the parameters of the Bragg grating. Consequently, monitoring the resonance frequency, a shift in resonance frequency, or other spectral characteristics or changes thereof over time allows exact temperature measurements to be performed. This may lead, e.g., to ultra-small footprint temperature sensors as a standalone device or to a combined sensor for temperature and ultrasound sensing for tissue ablation applications.

e. Frequency Differentiation Imaging

Due to the high mode confinement in some waveguides, it is possible to create ultra-miniaturized asymmetric optical resonators, having a structure as described above. Sub-micron sensor sizes result in an ultrabroad frequency response of the sensor of several hundreds of MHz. For example in the field of optoacoustic/photoacoustic imaging, the central frequency of the ultrasonic signals emitted from an absorber is proportional to its size. As a result, an asymmetric optical resonator allows the central frequencies to be resolved and to mark each of the absorbers according to its size. As complementary information, the frequency dependent attenuation of ultrasound in tissue allows one to also draw conclusions about the depth of the detected absorbers. These two levels of information allow a size and depth dependent contrast to be added to the optoacoustic modality in imaging applications as well as in biomedical sensing (as described in the exemplary use "b. Medical sensing device" above). By calculating time delays of ultrasonic signals, the speed of sound variations can be calculated, complementing the measurements with information of density and composition. For example, a spectral analysis of acquired ultrasonic signals from skin acquired by a point measurement can indicate on the density and depth of blood vessels.

f. Projection Imaging

Sub-micron sensor sizes will result in an ultra-high detection angle above 100°. This allows the method mentioned in exemplary use "e. Frequency differentiation imaging" to be employed for monitoring the vasculature properties over a large skin area of several mm$^2$ without the need of raster scanning.

The optical resonator is operated in optical reflection mode. The light 41 coupled into the optical resonator through the Bragg grating and the return light 42 coupled out from the optical resonator through the Bragg grating traverse the same segment of the waveguide in opposite directions. The waveguide with optical resonator may optionally be used in combination with an acoustic cavity that collects and focuses acoustic signals onto the waveguide with integrated optical resonator, as will be explained in more detail with reference to FIG. 12 to FIG. 14.

Figure 12:
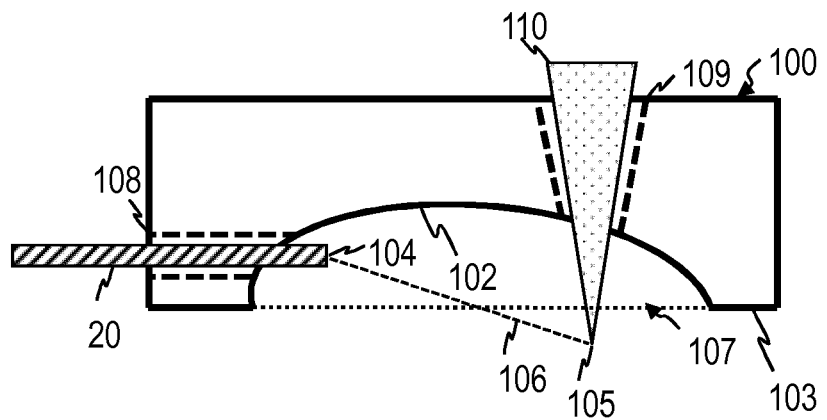
FIG. 12 is a schematic view of a sensor according to an embodiment.

FIG. 12 shows a sensor 10 according to an embodiment. The sensor 10 comprises an acoustic transducer and an acoustic mirror 100. The acoustic transducer may be configured as a waveguide 20 that may have any one of the configurations explained with reference to FIG. 1 to FIG. 11 above. The waveguide may comprise an optical resonator adjacent an end face of the waveguide 20, with the optical resonator being formed by a Bragg grating on one side and at least one reflector that is not identical to the Bragg grating on the opposite side, with an inner portion of the optical resonator extending therebetween. Other acoustic transducers may be used.

The acoustic mirror 100 has an acoustic reflecting surface 102 that is shaped like part of the surface of a rotational ellipsoid. The acoustic reflecting surface 102 is a boundary of an acoustic cavity 107 that is recessed relative to a face surface 103 of the acoustic mirror 100. The face surface 103 may be planar or may otherwise define a plane. For illustration, the face surface 103 may have an annular portion for abutment on a specimen, which annular surface may define a reference plane for the orientation of the acoustic reflecting surface 102 that forms part of a rotational ellipsoid.

The acoustic mirror 100 is generally configured to collect and focus acoustic signals onto an ultrasound transducer installed inside the cavity.

The acoustic mirror 100 enables the implementation of reflection-mode optoacoustic sensing in applications and devices that were not accessible before, e.g. due to size and geometry constraints. The acoustic mirror 100 includes an ellipsoidal acoustic cavity 107 with two acoustic focal volumes, also referred to as "acoustic foci." The acoustic foci may be located at the focal points 104, 105 of the rotational ellipsoid that defines the reflection surface 102. The ellipsoidal acoustic cavity 107 is configured in a way that a first focus 104 is inside the acoustic cavity 107 and a second focus 105 is outside the acoustic cavity 107.

When an acoustic source is positioned at or near the second, outer focus 105, for example, its acoustic signals will be collected and projected onto the first, inner focus 104 inside the cavity 107. At this first, inner focus 104, the acoustic transducer is positioned and records the amplified acoustic signals.

A retaining mechanism may position the acoustic transducer relative to the acoustic mirror 100. For illustration, the retaining mechanism may comprise a passage 108 extending through the acoustic mirror 100 from a side surface thereof to the acoustic cavity 107. The acoustic transducer may be retained by the passage 108 so as to position the acoustic transducer in proximity to, preferably in overlapping relationship with the first focus 104.

Other retaining mechanisms may also be used.

An important aspect of the acoustic mirror 100 is that a major axis 106 of the ellipsoid is tilted, e.g. relative to the plane defined by the face surface 103. This allows acoustic waves from outside the acoustic cavity 107 to be focused at the first focus 104 inside the acoustic cavity 107, where they are picked up by the acoustic transducer.

An angle between the major axis 106 and the plane defined by the face surface 103 may be equal to or greater than 5°, in particular equal to or greater than 10°, in particular equal to or greater than 12°. The maximum tilt angle between the major axis 106 relative to the plane defined by the face surface 103 may be 90°.

The acoustic mirror 100 may allow an optoacoustic excitation beam 110 to enter the acoustic cavity through a second aperture 109 and pass through it with the beam path not coinciding with the acoustic transducer installed at the first focus 104 of the ellipsoid, effectively decoupling the excitation path from the acoustic path. Alternatively, the acoustic mirror 100 can be manufactured of, or may comprise, an optically transparent material to allow the excitation beam 110 to be transmitted through the acoustic mirror 100 without the need of a second aperture. In this case, correction optics for possible optical diffraction due to the shape of the acoustic mirror 100 needs to be implemented. The excitation beam may be light, other electromagnetic radiation, or a particle beam.

A significant difference in the acoustic impedance of the acoustic mirror 100 and a coupling medium that can be provided in the acoustic cavity 107 can guarantee a high acoustic reflectivity. For applications that do not allow the use of metallic components, such as the novel field of magnetoacoustic imaging or measurements in close proximity to electromagnetic fields, the acoustic cavity can be created out of non-metallic materials, such as plastics (e.g., PVC).

The acoustic transducer may be a piezoelectric element, a capacitive transducer (CMUT), or an optical ultrasound transducer. In particular, the acoustic transducer may comprise the waveguide with integrated optical resonator in accordance with any one of the embodiments disclosed herein, and as described in more detail with reference to FIG. 1 to FIG. 11.

The acoustic mirror 100 with the aperture 108 for allowing the acoustic transducer to pass into the acoustic cavity 107 allows for an epi-illumination geometry for photoacoustic/optoacoustic sensing in various applications such as biomedical imaging, medical sensing and non-destructive testing.

The sensor comprising the acoustic mirror 100 addresses a common limitation to optoacoustic sensing, which is caused by the requirement to excite an optoacoustic signal in a given volume and to simultaneously interrogate the same volume by an acoustic transducer. Especially for micron-sized objects in optoacoustic imaging and non-destructive testing (NDT), this is highly relevant due to physical limitations in transducer size and setup geometries. The size of conventional sensitive acoustic transducers commonly prevents excitation and acoustic detection to be performed from the same side of a given sample. Consequently, optoacoustic sensing is usually performed in transmission mode geometries, limiting applications to thin samples.

By contrast, the acoustic mirror 100 allows excitation and optoacoustic sensing to be performed in reflection mode, where the excitation beam 110 and the acoustic transducer are located on the same side of the specimen. The excitation beam 110 for optoacoustic excitation may enter the acoustic mirror 100 through its aperture 109 in its bottom and travel through the acoustic cavity 107. A focus of the beam 110 may coincide with the second, outer focus 105 of the acoustic mirror 100, although it is not required that the excitation energy is focused. Acoustic signals generated by the excitation beam 100 are collected by the acoustic mirror 100 and focused onto the first, inner focus 104 where the acoustic transducer is positioned to record the amplified acoustic signals.

The sensor explained with reference to FIG. 12 has a wide variety of applications, some of which are described below:

a. Optoacoustic Imaging

Optoacoustic microscopy (OAM) as well as OA tomography (OAT) record images of absorption contrast of organic and non-organic specimens based on the photoacoustic effect. In microscopy, it is desirable to implement this powerful and label-free optical modality in addition to existing microscopy modalities, such as confocal microscopy and multi-photon fluorescence microscopy. Yet, the need for transmission mode geometry and the interference of the acoustic mirror with the excitation beam path in reflection mode are currently limiting factors. The acoustic mirror 100 overcomes these hurdles without cutbacks in terms of sensitivity and bandwidth compared to sensors currently implemented in transmission mode geometries. By this, the acoustic mirror 100 enables a simple implementation of OAM and OAT into standard multimodal microscopy setups. In case of water immersion objectives, the coupling medium would extend through the aperture and an adapter may seal the interface to the microscope objective. Microactuators may be introduced to the adapter in order to adjust the position of the outer acoustic focus relative to the optical focus. The optical focus can be scanned by galvanometric mirrors along the outer acoustic plane.

b. Non-Invasive Medical Sensor

In OA spectroscopy, a photoacoustic spectrum of a given specimen is recorded by observing the optical absorption and its emitted acoustic signal at different optical wavelengths. This method can be applied to investigate biomedical samples as well as to study the composition of solids, liquids and gases in environmental sensing. As a biomedical application, the miniature size and design of the acoustic mirror 100 allows for sensors to be embedded in portable devices. By matching the acoustic mirror 100 with cost effective illumination (e.g. laser diodes) and USTs (such as piezoelectric elements or the waveguides with integrated optical resonators explained with reference to FIG. 1 to FIG. 11), this combination enables the broad application of OA in medical devices. A medical sensor enabled by the acoustic mirror 100 could then be applied in home/remote monitoring applications, allowing for early warning of diseases and on-going monitoring of disease progression. Sensing the biochemical structure and biophysical parameters of skin, i.e., from blood and vasculature, diagnoses about cardiovascular diseases as well as about diabetes conditions can be made.

Figure 13:
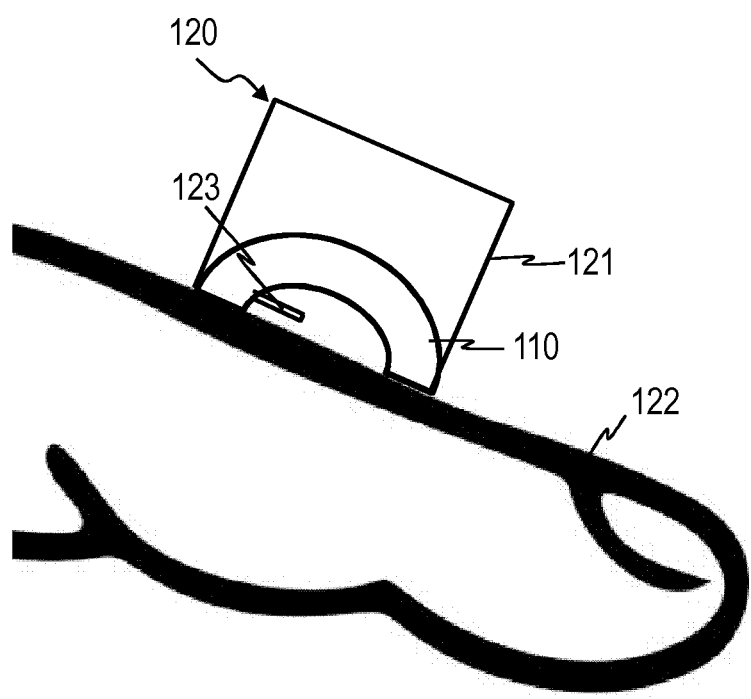
FIG. 13 is a schematic view illustrating an exemplary use of the sensor of FIG. 12.

FIG. 13 depicts the working principle of such a sensor 120. The sensor comprises an acoustic mirror 100, an acoustic transducer 123, and a retaining mechanism for positioning the acoustic transducer 123 relative to the acoustic mirror 100. A housing 121 may house further components, such as a laser diode. Physiological information of tissue and vasculature is acquired via the acoustic transducer through optoacoustic imaging and spectroscopy of a finger 122.

The acoustic mirror 100 may be used as basis for a non-invasive multi-modal medical sensor. The acoustically matched and optically transparent acoustic mirror 100 is in contact with the human finger 122 through an aperture. The excitation beam leaves the light source and impinges onto the specimen 122. The generated acoustic signals are collected and projected onto an acoustic transducer 123 positioned to overlap with the inner acoustic focus 104. Optical or electrical input and output contacts for the acoustic transducer can transverse trough the acoustic mirror 100.

c. Optoacoustic Non-Destructive Testing (NDT)

Similar to the well-established field of laser ultrasonic NDT, OA NDT is a big step forward to detecting flaws in processed materials and equipment. One of the major reasons why OA NDT has not been widely applied, yet, is the lack of mobility and the need for a transmission mode geometry with current. This shortcoming is overcome with the use of the acoustic mirror 100. The acoustic mirror 100 enables OA NDT. For example, when testing complex materials such as carbon composites, the high sensitivity and higher frequency content of the acoustic mirror 100 with its acoustic transducer—compared to purely piezoelectric sensors—is beneficial as the amplitude of the ultrasonic signals emitted from such small absorbers is small.

Figure 14:
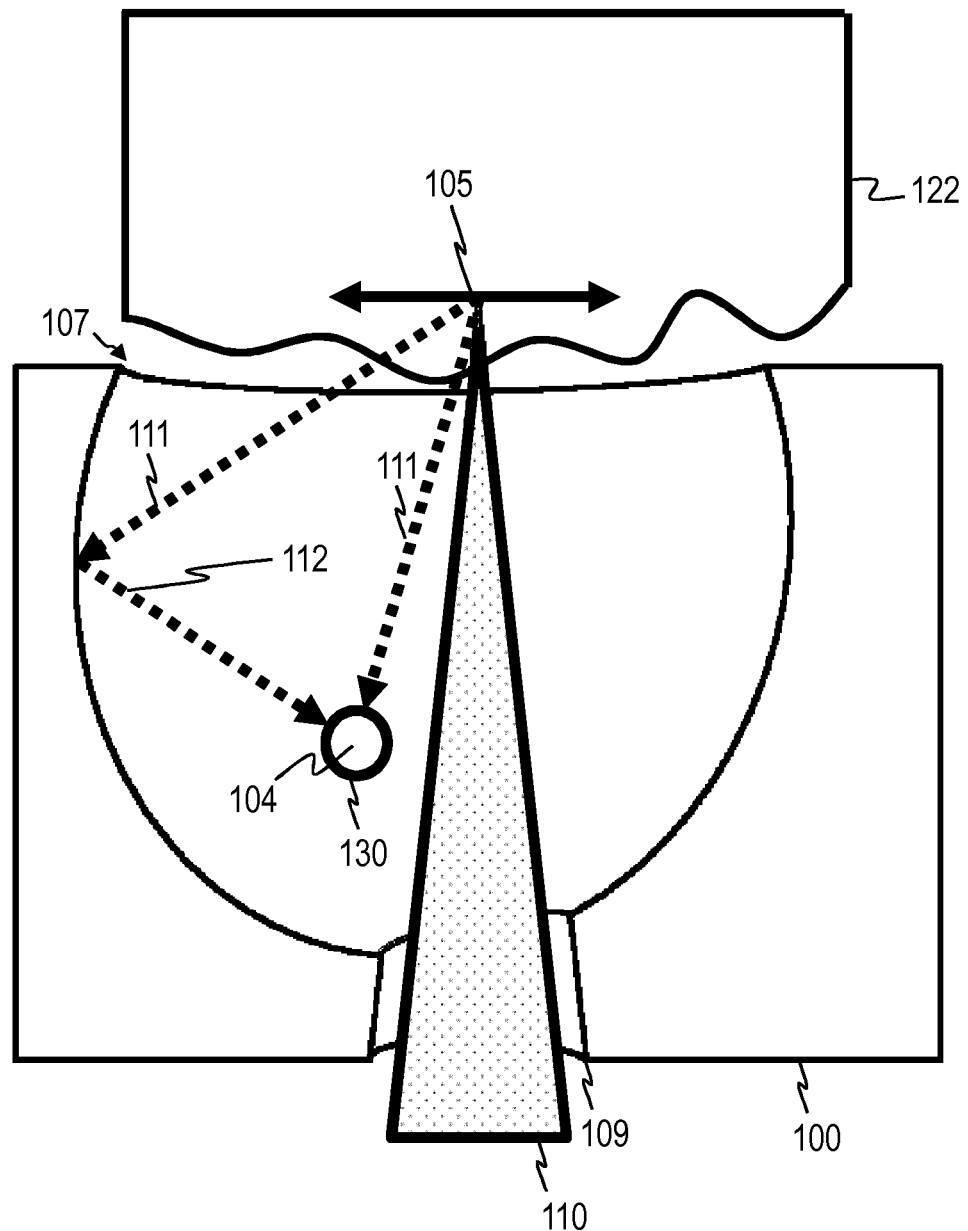
FIG. 14 is a schematic view of a sensor according to an embodiment.

The concept of the acoustic mirror 100 was tested in an OA microscopy experiment. Here, the size of the acoustic mirror as depicted in FIG. 14 was as little as 10 mm×8 mm, and the acoustic cavity 107 was filled with an acoustic coupling medium such as water or ultrasound gel and sealed by thin PE foil as optically transparent medium. The acoustic cavity 107 was CNC carved out of hardened stainless steel for high reflection coefficients when applied in water. The optical focus of the excitation beam 110 coincided with the outer acoustic focus 105 and an optical UST 130 based on a phase shifter Bragg grating (π-FBG) was located at the inner acoustic focus 104. The inner acoustic focus 104 may be located within or align with the optical UST 130, as schematically shown in FIG. 14.

The performance of the acoustic mirror 100 has been tested in multiple experiments in an OA microscopy setup. The characterization has been performed with an optoacoustic signal generated by a pulsed laser operating at a wavelength of 515 nm and a 2 kHz repetition rate and an absorber positioned at the outer acoustic focus of the cavity. The acoustic signal amplification was found to be in the order of 7 dB, while its bandwidth was not affected by the acoustic mirror 100. In conclusion, the acoustic mirror 100 allowed for epi-illumination OA microscopy in a multi-modal setup and simultaneous Second-harmonic imaging (SHG) microscopy.

Figure 15:
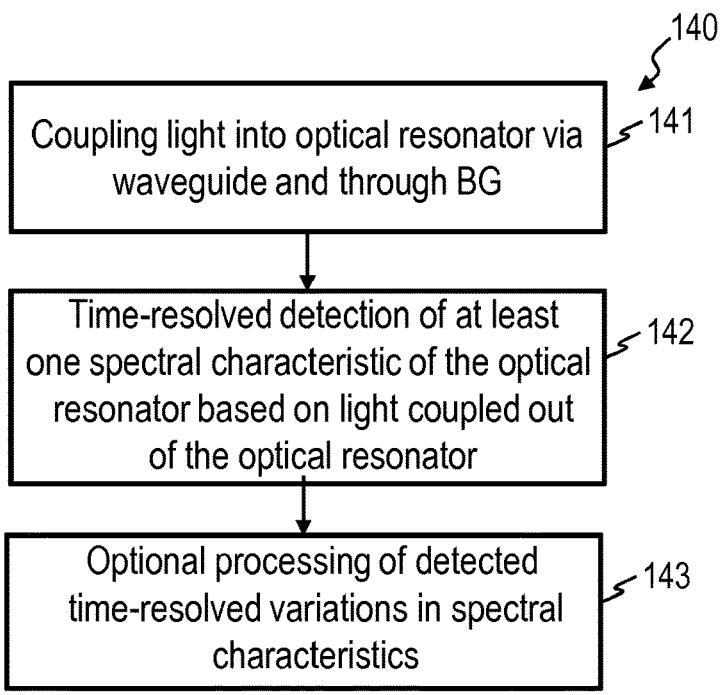
FIG. 15 is a flow chart of a method according to an embodiment.

FIG. 15 is a flow chart of a method 140 according to an embodiment. The method 140 may be performed using any one of the sensors disclosed herein that comprise a waveguide with an integrated optical resonator, which is formed by a Bragg grating on one side, by at least one reflector that is different in construction from the Bragg grating on the other side, and an inner portion of the optical resonator extending therebetween.

At step 141, light is coupled into the optical resonator via the Bragg grating.

At step 142, at least one spectral characteristic of the optical resonator or a change of at least one spectral characteristic of the optical resonator is detected. The at least one spectral characteristic or change of at least one spectral characteristic can include an intensity of the outgoing light, at a fixed frequency, that is coupled out of the optical resonator. The at least one spectral characteristic can include one or several resonance frequencies of the optical resonator. The at least one spectral characteristic or change of at least one spectral characteristic can include an intensity or intensity change indicative of a shift of one or several resonance frequencies of the optical resonator. The at least one spectral characteristic or change of at least one spectral characteristic can include a spectral response measured for a plurality of frequencies. The detection may be carried out in a time-resolved manner.

At step 143, time-dependent variations in the spectral characteristics may be used for further analysis or processing. For illustration, the time-dependent variations in the spectral characteristics may be used may be used to perform at least one of the following: acoustic sensing; medical sensing; bio sensing; temperature sensing; frequency differentiation imaging; projection imaging; optoacoustic imaging; optoacoustic non-destructive testing; chemical sensing; plasmonic sensing.

The small size of sensors according to embodiments facilitates combining several sensors into a sensor array.

Figure 16:
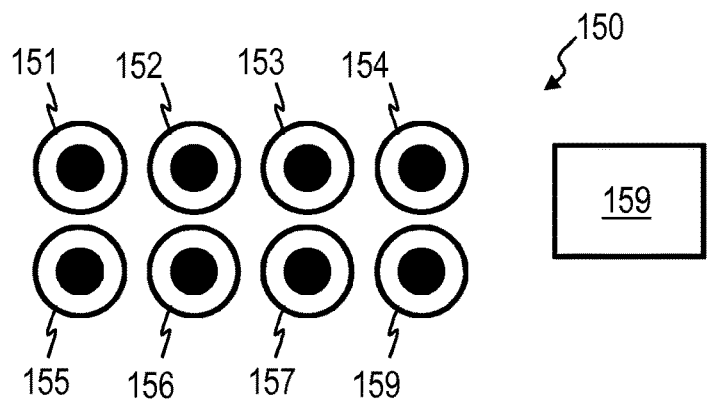
FIG. 16 is a schematic view of a sensor array according to an embodiment.

FIG. 16 is a schematic view of a sensor array 150 according to an embodiment. A plurality of waveguides 151-158 that respectively comprise an integrated optical resonator may be provided in a one- or two-dimensional array. A read-out mechanism 159 may read out at least one spectral characteristic of the optical resonators or a change of at least one spectral characteristic of the optical resonators of the various waveguides 151-158, either simultaneously or time-sequentially. The end faces of the plurality of waveguides 151-158 may be arranged side-by-side in a co-planar configuration.

Figure 17:
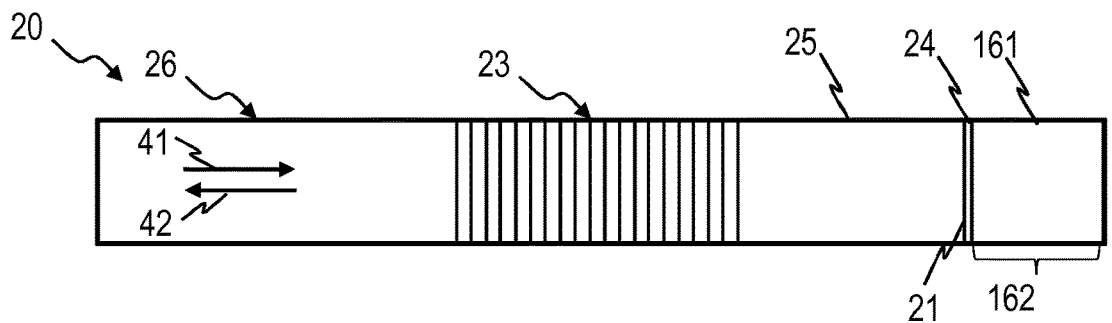
FIG. 17 is a schematic view of a waveguide with integrated optical resonator according to an embodiment.

FIG. 17 is a schematic view of a waveguide with integrated optical resonator according to an embodiment.

In any one of the waveguides described above, an acoustic coupling element 161 may be attached to the end face of the waveguide. The acoustic coupling element 161 may be a cell. The acoustic coupling element 161 may be of any shape and any material, and may be selected so as to perform acoustic impedance matching, for example, between the optical resonator and the environment in which sensing is to be performed. A length 162 of the acoustic coupling element may be chosen to match one or several central frequencies of acoustic waves for which sensing is to be performed. Depending on the desired wavelength, the length 162 of the acoustic coupling element may be between 1 μm and 10 cm, preferably between 2 μm and 1 cm, more preferably between 3 μm and 5 mm.

It will be appreciated that the acoustic coupling element 161 is not shown to scale in FIG. 17. Typically, the length 162 of the acoustic coupling element 161 will significantly exceed the length of the optical resonator.

The following embodiments are also disclosed:

Embodiment 1: A sensor, comprising:
a waveguide having a longitudinal axis and an end face, the waveguide comprising a Bragg grating; and
at least one reflector on the end face of the waveguide,
wherein an optical resonator is formed by the Bragg grating, the at least one reflector, and an inner portion of the optical resonator between the Bragg grating and the at least one reflector,
wherein the inner portion of the optical resonator extends within a portion of the waveguide.

Embodiment 2: The sensor of embodiment 1, wherein the optical resonator is configured to confine electromagnetic radiation in proximity to the end face, optionally wherein the optical resonator is configured to confine electromagnetic radiation within a portion of the waveguide that extends a distance in a range from 100 nm to 1 cm, preferably from 200 nm to 5 mm, from the end face.

Embodiment 3: The sensor of embodiment 1 or embodiment 2, wherein the sensor is an acoustic sensor, a pressure sensor, or a temperature sensor.

Embodiment 4: The sensor of any one of embodiments 1 to 3, further comprising a detector configured to detect at least one spectral characteristic or a change of at least one spectral characteristic of the optical resonator; optionally wherein the at least one spectral characteristic or change of at least one spectral characteristic may comprise any one, or any combination of: at least one resonance frequency of the optical resonator; a shift of at least one resonance frequency of the optical resonator; an intensity of detected light in response to interrogating light measured using coherent continuous wave (cw) interferometry or incoherent cw interferometry; a spectral response of the optical resonator; and/or a bandwidth of at least one resonance peak of the optical resonator.

Embodiment 5: The sensor of embodiment 4, wherein the sensor further comprises a source configured to supply electromagnetic radiation to the optical resonator through the Bragg grating, and wherein the detector is configured to detect electromagnetic radiation passing from the optical resonator through the Bragg grating and propagating along the waveguide, optionally wherein the source outputs light at a wavelength selected such that the light acquires a phase that is approximately a or an integer multiple of π upon passage through the inner portion of the optical resonator from the Bragg grating to the at least one reflector, and/or that a total round trip phase shift in the inner portion of the optical resonator is approximately π or an odd multiple of π.

Embodiment 6: The sensor of embodiment 5, wherein the waveguide has a second end opposite the end face, the end face and the second end being spaced along the longitudinal axis, and both the source of electromagnetic radiation and the detector are coupled to the second end of the waveguide.

Embodiment 7: The sensor of any one of embodiments 4 to 6, wherein the detector is configured to sense a spectral response of the optical resonator.

Embodiment 8: The sensor of any one of embodiments 4 to 7, wherein the detector is configured to sense a plurality of resonance frequencies of the optical resonator.

Embodiment 9: The sensor of any one of embodiments 4 to 8, wherein the detector is configured to sense an intensity of electromagnetic radiation from the optical resonator as a function of time.

Embodiment 10: The sensor of any one of embodiments 4 to 9, wherein the detector is configured to sense a change in spectral response or a change in intensity of light coupled out of the optical resonator, optionally wherein the detector is configured to sense the change in spectral response or change in intensity as a function of time.

Embodiment 11: The sensor of embodiment 10, wherein the detector is configured to sense the change in spectral response or change in intensity triggered by at least one of:
a change in distance between the Bragg grating and the at least one reflector;
a change in refractive index in the portion of the waveguide;
a change in reflectivity of the Bragg grating.

Embodiment 12: The sensor of any one of the preceding embodiments, wherein the waveguide is selected from a group consisting of: an integrated photonic circuit, a single mode waveguide, a multimode waveguide, a polarization maintaining waveguide, a non-polarization maintaining waveguide, a mode composite waveguide, a photonic crystal fiber.

Embodiment 13: The sensor of any one of the preceding embodiments, wherein the waveguide is an optical fiber, the Bragg grating is a fiber Bragg grating, and the at least one reflector comprises an optically reflective layer.

Embodiment 14: The sensor of any one of the preceding embodiments, wherein the waveguide is a silicon waveguide.

Embodiment 15: The sensor of embodiment 14, wherein the Bragg grating comprises corrugations formed along side walls of the silicon waveguide.

Embodiment 16: The sensor of embodiment 14 or embodiment 15, wherein the waveguide is a silicon-on-insulator waveguide.

Embodiment 17: The sensor of any one of the preceding embodiments, wherein the at least one reflector comprises at least one reflective layer.

Embodiment 18: The sensor of embodiment 17, wherein the at least one reflective layer comprises t least one metallic layer and/or at least one dielectric layer.

Embodiment 19: The sensor of embodiment 17 or embodiment 18, wherein the at least one reflective layer is coated directly onto the end face of the waveguide.

Embodiment 20: The sensor of embodiment 17 or embodiment 18, wherein the at least one reflective layer is coated onto a carrier different from the waveguide.

Embodiment 21: The sensor of any one of the preceding embodiments, wherein the at least one reflector comprises particles or a material configured such that surface plasmons are generated therein to form the optical resonator with the Bragg grating, at least one resonance frequency of the optical resonator being shifted in response to interaction of a specimen with the particles or material, optionally wherein the particles or material comprise at least one of: metallic nanoparticles, dielectric elements, or structured metallic layers.

Embodiment 22: The sensor of any one of the preceding embodiments, wherein the at least one reflector comprises at least one additional optical structure integrated in the waveguide.

Embodiment 23: The sensor of embodiment 22, wherein the at least one additional optical structure is disposed in proximity to the end face, interposed between the end face and the Bragg grating.

Embodiment 24: The sensor of any one of the preceding embodiments, wherein the waveguide extends only from a side of the optical resonator at which the Bragg grating delimits the optical resonator.

Embodiment 25: The sensor of any one of the preceding embodiments, wherein the optical resonator is an asymmetric optical resonator delimited by the Bragg grating and the at least one reflector on opposite sides, the Bragg grating and the at least one reflector having different constructions.

Embodiment 26: The sensor of any one of the preceding embodiments, further comprising an acoustic mirror and a retaining mechanism for positioning the optical resonator relative to the acoustic mirror.

Embodiment 27: The sensor of embodiment 26, wherein the acoustic mirror comprises a surface that defines at least a portion of a rotational ellipsoid.

Embodiment 28: The sensor of embodiment 27, wherein a major axis of the rotational ellipsoid is tilted with respect to a face surface of the acoustic mirror.

Embodiment 29: The sensor of embodiment 28, wherein the surface that defines at least a portion of the rotational ellipsoid is recessed from the face surface.

Embodiment 30: The sensor of embodiment 28 or embodiment 29, wherein the face surface is a planar face surface.

Embodiment 31: The sensor of any one of embodiments 26 to 30, wherein the retaining mechanism is configured to position the waveguide such that the waveguide overlaps a focal point of the rotational ellipsoid or is located in proximity to the focal point of the rotational ellipsoid.

Embodiment 32: The sensor of embodiment 31, wherein the retaining mechanism is configured to position waveguide such that the optical resonator overlaps the focal point of the rotational ellipsoid or is located in proximity to the focal point of the rotational ellipsoid.

Embodiment 33: The sensor of embodiment 31 or embodiment 32, wherein the focal point is located within an acoustic cavity of the acoustic mirror.

Embodiment 34: The sensor of any one of embodiments 31 to 33, wherein a further focal point of the rotational ellipsoid is located outside the acoustic cavity of the acoustic mirror.

Embodiment 35: The sensor of any one of embodiments 26 to 34, wherein the retaining mechanism comprises a retaining passage in the acoustic mirror through which the waveguide extends.

Embodiment 36: The sensor of any one of embodiments 26 to 35, wherein the acoustic mirror is fully or partially transparent to electromagnetic radiation.

Embodiment 37: The sensor of any one of embodiments 26 to 36, wherein the acoustic mirror is fully or partially transparent to light.

Embodiment 38: The sensor of any one of the preceding embodiment, further comprising an excitation source configured to provide excitation energy to a specimen, optionally wherein the excitation source is configured to provide excitation energy that triggers emission of acoustic waves upon impingement on the specimen, the sensor being configured to sense pressure variations induced by the acoustic waves.

Embodiment 39: The sensor of embodiment 38, wherein the excitation source comprises at least one of a laser, a source of electromagnetic radiation, or a particle source.

Embodiment 40: The sensor of embodiment 38 or embodiment 39 when dependent on any one of embodiments 26 to 37, wherein the acoustic mirror comprises an excitation passage extending through the acoustic mirror, the excitation source being configured to supply the excitation energy to the specimen through the excitation passage; and/or wherein the acoustic mirror comprises a portion transparent to the excitation energy.

Embodiment 41: The sensor of any one of the preceding embodiments, further comprising an acoustic coupling element attached to the end face of the waveguide, optionally wherein the acoustic coupling element has a length chosen to match a central frequency of an acoustic wave that is to be sensed, optionally wherein the acoustic coupling element has a length of between 1 µm and 10 cm.

Embodiment 42: A sensor array, comprising a plurality of sensors according to any one of the preceding embodiments.

Embodiment 43: The sensor array of embodiment 42, wherein the plurality of sensors are arranged in one-dimensional array or in a two-dimensional array.

Embodiment 44: The sensor array of embodiment 42 or embodiment 43, wherein the sensor array is operative to perform spatially-resolved and time-resolved sensing of pressure variations, of temperature variations, or of plasmons.

Embodiment 45: The sensor array of any one of embodiments 42 to 44, wherein the sensor array is operative to perform acoustic imaging, in particular ultrasound imaging.

Embodiment 46: The sensor array of any one of embodiments 42 to 45, wherein the sensor array is operative to perform pressure imaging or temperature imaging.

Embodiment 47: The sensor array of any one of embodiments 42 to 46, further comprising a read-out mechanism configured to read out the plurality of sensors.

Embodiment 48: The sensor array of embodiment 47, wherein the read-out mechanism is configured to read out the optical resonator of each one of the plurality of sensors.

Embodiment 49: The sensor array of embodiment 47 or embodiment 48, wherein the read-out mechanism is configured to simultaneously read out the plurality of sensors.

Embodiment 50: The sensor array of embodiment 47 or embodiment 48, wherein the read-out mechanism is configured to time-sequentially read out the plurality of sensors.

Embodiment 51: A sensing method, comprising:
positioning a sensor relative to a specimen, wherein the sensor comprises:
a waveguide having a longitudinal axis and an end face, the waveguide comprising a Bragg grating;
at least one reflector on the end face of the waveguide;
wherein an optical resonator is formed by the Bragg grating, the at least one reflector, and an inner portion of the optical resonator between the Bragg grating and the at least one reflector, the inner portion of the optical resonator extending within a portion of the waveguide; and
detecting at least one spectral characteristic of the optical resonator or a change of at least one spectral characteristic of the optical resonator.

Embodiment 52: The sensing method of embodiment 51, wherein the at least one spectral characteristic or change of at least one spectral characteristic may comprise any one, or any combination of: at least one resonance frequency of the optical resonator; a shift of at least one resonance frequency of the optical resonator; an intensity of detected light in response to interrogating light measured using coherent continuous wave (cw) interferometry or incoherent cw interferometry; a spectral response of the optical resonator; and/or a bandwidth of at least one resonance peak of the optical resonator.

Embodiment 53: The sensing method of embodiment 51 or embodiment 52, wherein detecting the at least one spectral characteristic or the change of at least one spectral characteristic comprises detecting electromagnetic radiation passing through the Bragg grating.

Embodiment 54: The sensing method of any one of embodiments 51 to 53, further comprising providing electromagnetic radiation to the optical resonator through the Bragg grating.

Embodiment 55: The sensing method of any one of embodiments 51 to 54, wherein more than one resonance frequency of the optical resonator is detected.

Embodiment 56: The sensing method of any one of embodiments 51 to 55, further comprising determining a frequency and/or an intensity of acoustic waves incident on the optical resonator based on the detected at least one spectral characteristic or the detected change of at least one spectral characteristic.

Embodiment 57: The sensing method of any one of embodiments 51 to 56, further comprising determining a temperature or a temporal variation in temperature based on the detected at least one spectral characteristic or the detected change of at least one spectral characteristic.

Embodiment 58: The sensing method of any one of embodiments 51 to 57, further comprising processing determining a pressure or a temporal change in pressure based on the detected at least one spectral characteristic or the detected change of at least one spectral characteristic.

Embodiment 59: The sensing method of any one of embodiments 51 to 58, wherein the optical resonator confines light in proximity to the end face of the waveguide.

Embodiment 60: The sensing method of any one of embodiments 51 to 59, wherein the spectral characteristic of the optical resonator changes in response to plasmons or surface plasmons of the specimen.

Embodiment 61: The sensing method of any one of embodiments 51 to 60, wherein the at least one spectral characteristic of the optical resonator or the change of at least one spectral characteristic the optical resonator is used to perform at least one of the following:
acoustic sensing;
medical sensing;
bio sensing;
temperature sensing;
frequency differentiation imaging;
projection imaging;
optoacoustic imaging;
optoacoustic non-destructive testing;
chemical sensing;
plasmonic sensing.

Embodiment 62: The sensing method of any one of embodiments 51 to 61, wherein the sensor is the sensor of any one of embodiments 1 to 41, or wherein the method uses the sensor array of any one of embodiments 42 to 50.

Embodiment 63: A waveguide with integrated optical resonator, wherein the waveguide has a longitudinal axis and an end face, comprising:
a Bragg grating in the waveguide; and
at least one reflector on the end face of the waveguide, wherein an optical resonator is formed by the Bragg grating, the at least one reflector, and an inner portion of the optical resonator between the Bragg grating and the at least one reflector, wherein the inner portion of the optical resonator extends within a portion of the waveguide.

Embodiment 64: The waveguide with integrated optical resonator of embodiment 63, wherein the optical resonator is configured to confine electromagnetic radiation in proximity to the end face.

Embodiment 65: The waveguide with integrated optical resonator of embodiment 63 or embodiment 64, wherein the waveguide is an integrated photonic circuit.

Embodiment 66: The waveguide with integrated optical resonator of any one of embodiments 63 to 65, wherein the waveguide is selected from a group consisting of: a single mode waveguide, a multimode waveguide, a polarization maintaining waveguide, a non-polarization maintaining waveguide, a mode composite waveguide, a photonic crystal fiber.

Embodiment 67: The waveguide with integrated optical resonator of any one of embodiments 63 to 66, wherein the waveguide is an optical fiber, the Bragg grating is a fiber Bragg grating, and the at least one reflector comprises an optically reflective layer.

Embodiment 68: The waveguide with integrated optical resonator of any one of embodiments 63 to 67, wherein the waveguide is a silicon waveguide.

Embodiment 69: The waveguide with integrated optical resonator of embodiment 68, wherein the Bragg grating comprises corrugations formed along side walls of the silicon waveguide.

Embodiment 70: The waveguide with integrated optical resonator of embodiment 68 or embodiment 69, wherein the waveguide is a silicon-on-insulator waveguide.

Embodiment 71: The waveguide with integrated optical resonator of any one of embodiments 63 to 70, wherein the at least one reflector comprises at least one reflective layer, and/or wherein the at least one reflector comprises at least one of: a functionalized surface, a structured metallic layer, reflective elements disposed within the waveguide adjacent the end face.

Embodiment 72: The waveguide with integrated optical resonator of embodiment 71, wherein the at least one reflective layer comprises at least one metallic layer and/or at least one dielectric layer, optionally wherein the at least one reflective layer is coated directly onto the end face of the waveguide or optionally wherein the at least one reflective layer is provided on a carrier different from the waveguide.

Embodiment 73: The waveguide with integrated optical resonator of any one of embodiments 63 to 72, wherein the at least one reflector comprises particles or a material configured such that surface plasmons are generated therein to form the optical resonator with the Bragg grating, the at least one spectral characteristic of the optical resonator being shifted in response to interaction of a specimen with the particles or material.

Embodiment 74: The waveguide with integrated optical resonator of embodiment 73, wherein the particles or material comprise at least one of: metallic nanoparticles, dielectric elements, or structured metallic layers.

Embodiment 75: The waveguide with integrated optical resonator of any one of embodiments 63 to 74, wherein the at least one reflector comprises at least one additional optical structure integrated in the waveguide.

Embodiment 76: The waveguide with integrated optical resonator of embodiment 75, wherein the at least one additional optical structure is disposed in proximity to the end face, interposed between the end face and the Bragg grating.

Embodiment 77: The waveguide with integrated optical resonator of any one of embodiments 63 to 76, wherein the waveguide extends only from a side of the optical resonator at which the Bragg grating delimits the optical resonator.

Embodiment 78: The waveguide with integrated optical resonator of any one of embodiments 63 to 77, wherein the optical resonator is an asymmetric optical resonator delimited by the Bragg grating and the at least one reflector on opposite sides, the Bragg grating and the at least one reflector having different constructions.

Embodiment 79: A sensor, comprising:
an acoustic transducer;
an acoustic mirror; and
a retaining mechanism for positioning the acoustic transducer relative to the acoustic mirror.

Embodiment 80: The sensor of embodiment 79, wherein the acoustic transducer comprises a waveguide having a longitudinal axis, and the sensor further comprises a source of electromagnetic radiation and/or a detector coupled to the waveguide.

Embodiment 81: The sensor of embodiment 79 or embodiment 80, wherein the acoustic mirror comprises a surface that defines at least a portion of a rotational ellipsoid.

Embodiment 82: The sensor of embodiment 81, wherein a major axis of the rotational ellipsoid is tilted with respect to a face surface of the acoustic mirror.

Embodiment 83: The sensor of embodiment 82, wherein the surface that defines at least a portion of the rotational ellipsoid is recessed from the face surface.

Embodiment 84: The sensor of embodiment 82 or embodiment 83, wherein the face surface is a planar face surface.

Embodiment 85: The sensor of any one of embodiments 81 to 84, wherein the retaining mechanism is configured to position the acoustic transducer such that the acoustic transducer overlaps with a focal point of the rotational ellipsoid or is located in proximity to the focal point of the rotational ellipsoid.

Embodiment 86: The sensor of embodiment 85, wherein the acoustic transducer comprises a waveguide, the waveguide comprises an optical resonator integrated in the waveguide, and the retaining mechanism is configured to position waveguide such that the optical resonator overlaps the focal point of the rotational ellipsoid or is located in proximity to the focal point of the rotational ellipsoid.

Embodiment 87: The sensor of embodiment 85 or embodiment 86, wherein the acoustic transducer comprises a waveguide and the retaining mechanism is configured to position the waveguide such that an end face of the waveguide overlaps the focal point of the rotational ellipsoid or is located in proximity to the focal point of the rotational ellipsoid.

Embodiment 88: The sensor of any one of embodiments 85 to 87, wherein the focal point is located within an acoustic cavity of the acoustic mirror.

Embodiment 89: The sensor of any one of embodiments 85 to 88, wherein a further focal point of the rotational ellipsoid is located outside the cavity of the acoustic mirror.

Embodiment 90: The sensor of any one of embodiments 79 to 89, wherein the retaining mechanism comprises a retaining passage in the acoustic mirror through which the acoustic transducer extends.

Embodiment 91: The sensor of any one of embodiments 79 to 90, wherein the acoustic mirror is fully or partially transparent to electromagnetic radiation, in particular light.

Embodiment 92: The sensor of any one of embodiments 79 to 91, wherein the acoustic transducer comprises a waveguide, and the waveguide comprises an optical resonator configured to confine electromagnetic radiation in proximity to an end face of the waveguide, the optical resonator being integrated into the waveguide.

Embodiment 93: The sensor of any one of embodiments 79 to 92, wherein the sensor is an acoustic sensor, a pressure sensor, or a temperature sensor.

Embodiment 94: The sensor of any one of embodiments 79 to 93, further the acoustic transducer comprises a waveguide and a detector coupled to the waveguide.

Embodiment 95: The sensor of embodiment 94, wherein the sensor further comprises a source configured to supply electromagnetic radiation into the waveguide along a first direction, and wherein the detector is configured to detect electromagnetic radiation propagating along the waveguide in a second direction opposite to the first direction.

Embodiment 96: The sensor of embodiment 95, wherein both the source of electromagnetic radiation and the detector are coupled to the same end of the waveguide.

Embodiment 97: The sensor of embodiments 95 or embodiment 96, wherein the waveguide comprises an optical resonator and the detector is configured to sense one or more resonance frequencies of the optical resonator.

Embodiment 98: The sensor any one of embodiments 95 to 97, wherein the waveguide comprises an optical resonator and the detector is configured to sense a spectral response of the optical resonator.

Embodiment 99: The sensor of any one of embodiments 94 to 98, wherein the waveguide comprises an optical resonator and the detector is configured to sense an intensity of electromagnetic radiation from the optical resonator as a function of time.

Embodiment 100: The sensor of any one of embodiments 94 to 99, wherein the waveguide comprises an optical resonator and the detector is configured to sense a change in spectral response of the optical resonator or change in intensity of light coupled out of the optical resonator.

Embodiment 101: The sensor of embodiment 100, wherein the detector is configured to sense the change in spectral response or change in intensity as a function of time.

Embodiment 102: The sensor of embodiment 100 or embodiment 101, wherein the detector is configured to sense the change in spectral response or change in intensity triggered by at least one of:
a change in length of the optical resonator;
a change in refractive index of the optical resonator;
a change in reflectivity of a reflector delimiting the optical resonator.

Embodiment 103: The sensor of any one of embodiments 94 to 102, wherein the waveguide is an integrated photonic circuit.

Embodiment 104: The sensor of any one of embodiments 94 to 103, wherein the waveguide is selected from a group consisting of: a single mode waveguide, a multimode waveguide, a polarization maintaining waveguide, a non-polarization maintaining waveguide, a mode composite waveguide, a photonic crystal fiber.

Embodiment 105: The sensor of any one of embodiments 94 to 104, wherein the waveguide is an optical fiber, the Bragg grating is a fiber Bragg grating, and the at least one reflector comprises an optically reflective layer.

Embodiment 106: The sensor of any one of embodiments 94 to 104, wherein the waveguide is a silicon waveguide.

Embodiment 107: The sensor of embodiment 106, wherein the waveguide is a silicon-on-insulator waveguide.

Embodiment 108: The sensor of any one of embodiments 94 to 107, further comprising at least one reflector on an end face of the waveguide positioned in a cavity of the acoustic mirror.

Embodiment 109: The sensor of embodiment 108, wherein the at least one reflector comprises at least one reflective layer.

Embodiment 110: The sensor of embodiment 109, wherein the at least one reflective layer comprises at least one metallic layer and/or at least one dielectric layer.

Embodiment 111: The sensor of embodiment 109 or embodiment 110, wherein the at least one reflective layer is coated directly onto the end face of the waveguide.

Embodiment 112: The sensor of embodiment 109 or embodiment 110, wherein the at least one reflective layer is coated onto a carrier different from the waveguide.

Embodiment 113: The sensor of any one of embodiments 108 to 112, wherein the at least one reflector comprises at least one additional optical structure integrated in the waveguide.

Embodiment 114: The sensor of embodiment 113, wherein the at least one additional optical structure is disposed in proximity to an end face of the waveguide.

Embodiment 115: The sensor of any one of embodiments 79 to 114, wherein the acoustic transducer comprises a waveguide, the waveguide comprising an optical resonator positioned adjacent an end face of the waveguide.

Embodiment 116: The sensor of embodiment 115, wherein the optical resonator is an asymmetric optical resonator delimited by a Bragg grating and at least one reflector on opposite sides, the Bragg grating and the at least one reflector having different constructions.

Embodiment 117: The sensor of any one of embodiments 79 to 116, further comprising an excitation source configured to provide excitation energy to a specimen.

Embodiment 118: The sensor of embodiment 117, wherein the excitation source is configured to provide excitation energy that triggers emission of acoustic waves upon impingement on the specimen, the sensor being configured to sense pressure variations induced by the acoustic waves.

Embodiment 119: The sensor of embodiment 117 or embodiment 118, wherein the excitation source comprises at least one of a laser, a source of electromagnetic radiation, or a particle source.

Embodiment 120: The sensor of any one of embodiments 117 to 119, wherein the acoustic mirror comprises an excitation passage extending through the acoustic mirror, the excitation source being configured to supply the excitation energy to the specimen through the excitation passage.

Embodiment 121: The sensor of any one of embodiments 79 to 120, wherein the sensor is a portable sensor, in particular a handheld sensor.

In any one of the embodiments disclosed herein that uses a waveguide with asymmetric optical resonator, the Bragg grating and the at least one reflector provided on opposite sides of the optical resonator are optically reflective. A periodicity of the Bragg grating may be matched to the length Le of the optical resonator inner portion, to ensure that the Bragg grating has high reflectivity at a resonance frequency of the optical resonator, with the resonance frequency being such that light acquires a phase shift that is approximately $\pi$ or an integer multiple of n upon passage through the inner portion of the optical resonator (i.e., when covering the distance from the surface of the Bragg grating that is closest to the end face and the surface of the at least one reflector that is disposed closest to the Bragg grating) and/or a total round trip phase shift in the inner portion the optical resonator is approximately $\pi$ or an odd multiple of $\pi$ (i.e., $\pi$, 3 $\pi$, 5 $\pi$, 7 $\pi$, etc.).

While embodiments have been described with reference to the drawings, various alterations and modifications may be implemented in other embodiments. For illustration, while embodiments have been described with reference to ultrasound sensing, the sensors according to embodiments are not limited thereto, but may be applied for a wide variety of different purposes.

The invention claimed is:

1. A sensor, comprising:
   a waveguide having a longitudinal axis and an end face, the waveguide comprising a Bragg grating;
   at least one reflector on the end face of the waveguide;
   wherein an optical resonator is formed by the Bragg grating, the at least one reflector, and an inner portion of the optical resonator between the Bragg grating and the least one reflector, the inner portion of the optical resonator extending within a portion of the waveguide; and
   a detector configured to detect at least one spectral characteristic of the optical resonator or a change of at least one spectral characteristic of the optical resonator.

2. The sensor of claim 1, wherein the sensor is an acoustic sensor, a pressure sensor or a temperature sensor.

3. The sensor of claim 1, wherein the optical resonator is configured to confine electromagnetic radiation in proximity to the end face.

4. The sensor of claim 1, wherein the sensor further comprises a source configured to supply electromagnetic radiation to the optical resonator through the Bragg grating, and
   wherein the detector is configured to detect electromagnetic radiation passing from the optical resonator through the Bragg grating and propagating along the waveguide.

5. The sensor of claim 4, wherein the detector is configured to sense at least one of:
   a spectral response of the optical resonator;
   a change in a spectral response of the optical resonator as a function of time;
   an intensity of electromagnetic radiation coupled out from the optical resonator; or
   a change in intensity of electromagnetic radiation coupled out from the optical resonator as a function of time.

6. The sensor of claim 4, wherein the detector is configured to sense a change in the intensity of the electromagnetic radiation at a fixed frequency.

7. The sensor of claim 1, wherein the at least one reflector comprises at least one reflective layer, optionally wherein the at least one reflective layer comprises at least one metallic layer and/or at least one dielectric layer coated directly onto the end face of the waveguide or onto a carrier different from the waveguide.

8. The sensor of claim 1, wherein the at least one reflector comprises particles or a material configured such that surface plasmons are generated therein to form the optical resonator with the Bragg grating, the at least one spectral characteristic being at least one resonance frequency of the optical resonator that is shifted in response to interaction of a specimen with the particles or material.

9. The sensor of claim 1, further comprising
   an acoustic coupling element attached to the end face of the waveguide, optionally wherein the acoustic coupling element has a length chosen to match a central frequency of an acoustic wave that is to be sensed.

10. The sensor of claim 1, further comprising
    an acoustic mirror and a retaining mechanism for positioning the optical resonator relative to the acoustic mirror.

11. The sensor of claim 10, wherein the acoustic mirror comprises a surface that defines at least a portion of a rotational ellipsoid, wherein a major axis of the rotational ellipsoid is tilted with respect to a face surface of the acoustic mirror, and wherein the surface that defines at least a portion of the rotational ellipsoid is recessed from the face surface.

12. The sensor of claim 10, wherein the retaining mechanism is configured to position the waveguide such that the waveguide overlaps a focal point of the rotational ellipsoid or is located in proximity to the focal point of the rotational ellipsoid.

13. The sensor of claim 12, wherein the focal point is located within an acoustic cavity of the acoustic mirror.

14. The sensor of claim 1, wherein the waveguide is an optical fiber.

15. The sensor of claim 1, wherein the waveguide is a silicon waveguide.

16. The sensor of claim 15, wherein the inner portion of the optical resonator has a length of less than 1 μm.

17. The sensor of claim 1, wherein the length of the inner portion of the optical resonator is shorter than a length of the Bragg grating.

18. The sensor of claim 1, wherein the optical resonator is adapted such that a phase shift of interrogating light upon passage through the inner portion is approximately $\pi$.

19. The sensor of claim 1, wherein the optical resonator is adapted such that a phase shift of interrogating light upon passage through the inner portion is approximately an odd integer multiple of $\pi$.

20. The sensor of claim 1, wherein the length of the inner portion of the optical resonator is matched to a periodicity of the Bragg grating, optionally wherein the length of the inner portion of the optical resonator is equal to one period of the Bragg grating or an integer multiple of one period of the Bragg grating.

21. The sensor of claim 1, wherein the inner portion of the optical resonator has a length of less than 100 µm.

22. The sensor of claim 1, wherein the waveguide has a core and a cladding, wherein the cladding extends over and surrounds the inner portion of the optical resonator.

23. A sensor array, comprising:
a plurality of sensors according to claim 1, optionally wherein the plurality of sensors are arranged in one-dimensional array or in a two-dimensional array.

24. A sensing method, comprising:
positioning a sensor relative to a specimen, wherein the sensor comprises:
a waveguide having a longitudinal axis and an end face, the waveguide comprising a Bragg grating;
at least one reflector on the end face of the waveguide; and
wherein an optical resonator is formed by the Bragg grating, the at least one reflector, and an inner portion of the optical resonator between the Bragg grating and the least one reflector, wherein the inner portion of the optical resonator extends within a portion of the waveguide; and
detecting at least one spectral characteristic of the optical resonator or a change of at least one spectral characteristic of the optical resonator.

25. The sensing method of claim 24, wherein the detected at least one spectral characteristic of the optical resonator or the change of the at least one spectral characteristic of the optical resonator is used to perform at least one of the following:
acoustic sensing;
medical sensing;
bio sensing;
temperature sensing;
frequency differentiation imaging;
projection imaging;
optoacoustic imaging;
optoacoustic non-destructive testing;
chemical sensing; or
plasmonic sensing.

* * * * *